US006974867B2

(12) United States Patent
Wu et al.

(10) Patent No.: US 6,974,867 B2
(45) Date of Patent: Dec. 13, 2005

(54) COMPOSITIONS AND METHODS FOR TREATING NEOPLASTIC DISEASE USING CHEMOTHERAPY AND RADIATION SENSITIZERS

(75) Inventors: Bin Wu, El Cerrito, CA (US); Todd W. Seeley, Moraga, CA (US); Lewis T. Williams, Mill Valley, CA (US)

(73) Assignee: Chiron Corporation, Emeryville, CA (US)

( * ) Notice: Subject to any disclaimer, the term of this patent is extended or adjusted under 35 U.S.C. 154(b) by 0 days.

(21) Appl. No.: 09/870,937

(22) Filed: May 30, 2001

(65) Prior Publication Data

US 2002/0049180 A1 Apr. 25, 2002

Related U.S. Application Data

(60) Provisional application No. 60/208,435, filed on May 31, 2000.

(51) Int. Cl.$^7$ ................................................. C07H 21/04
(52) U.S. Cl. ...................... 536/24.1; 536/23.1; 514/44; 424/9.2
(58) Field of Search ............................. 536/23.1, 24.1; 514/44; 424/9.2

(56) References Cited

U.S. PATENT DOCUMENTS 5,700,637 A * 12/1997 Southern ..................... 435/6
6,087,485 A * 7/2000 Brooks-Wilson et al. .. 536/23.5

FOREIGN PATENT DOCUMENTS

| WO | WO 98/06437 | 2/1998 |
| WO | WO 99/08711 | 2/1999 |
| WO | WO99/65928 | 12/1999 |
| WO | WO 01/16306 A2 | 3/2001 |

OTHER PUBLICATIONS

Anderson, F. Human gene therapy. Nature 392:26–30, 1998.*
Verma et al. Gene therapy–promises, problems and prospects. Nature 389: 239–242, 1997.*
Mountain, A. Gene therapy: first decade. TIBTECH 18: 119–128, 2000.*
Branch, A. A good antisense molecule is hard to find. TIBS 23: 45–50, 1998.*
Jen K, et al. Suppression of gene expression by targeted disruption of messenger RNA: available options and current strategies. Stem Cells 18: 307–319, 2000.*
Banin et al., "Enhanced Phosphorylation of p53 by ATM in Response to DNA Damage," *Science* 281(5383):1674–1677, Sep. 11, 1998.
Boulton et al., "Wortmannin is a Potent Inhibitor of DNA Double Strand Break but not Single Strand Break Repair in Chinese Hamster Ovary Cells," *Carcinogenesis (Lond.)* 17(11):2285–2290, Nov. 1996.
Canman et. al., "Activation of the ATM Kinase by Ionizing Radiation and Phosphorylation of p53," *Science* 281(5383):1677–1679, Sep. 11, 1998.
Chen et al., "Identification of Ataxia Telangiectasia Heterozygotes, a Cancer Prone Population," *Nature* 274(5670):484–486, Aug. 3, 1978.
Chernikova et al., "Wortmannin Sensitizes Mammalian Cells to Radiation by Inhibiting the DNA–dependent Protein Kinase–Mediated Rejoining of Double–strand Breaks," *Radiation Research* 151(2):159–166, Feb. 1999.
Cox et al., "Tumour Suppressors, Kinases and Clamps: how p53 Regulates the Cell Cycle in Response to DNA Damage," *Bioessays* 17(6):501–508, Jun. 1995.
El–Deiry "Regulation of p53 Downstream Genes," *Seminars in Cancer Biology* 8(5):345–357, 1998.
Elledge et al., "A Question of Balance: The Role of Cyclin–Kinase Inhibitors in Development and Tumorigenesis," *Trends in Cell Biology* 6:388–393, Oct. 1996.
Fiscella et al., "Mutation of the Serine 15 Phosphorylation Site of Human p53 Reduces the Ability of p53 to Inhibit Cell Cycle Progression," *Oncogene* 8(6):1519–1528, Jun. 1993.
Haupt et al., "Mdm2 Promotes the Rapid Degradation of p53," *Nature* 387(6630):296–299, May 15, 1997.
Hendry et al., "P53 Deficiency Produces Fewer Regenerating Spermatogenic Tubules after Irradiation," *International J. of Radiation Biology* 70(6):677–682, Dec. 1996.
Hosoi et al., "A Phosphatidylinositol 3–Kinase Inhibitor Wortmannin Induces Radioresistant DNA Synthesis and Sensitizes Cells to Bleomycin and Ionizing Radiation," *International J. of Cancer* 78(5):642–647, Nov. 23, 1998.
Huang et al., "Lipitoids—novel Cationic Lipids for Cellular Delivery of Plasmid DNA in vitro," *Chemistry & Biology* 5(6):345–354, Jun. 1998.
Kastan et al., "A Mammalian Cell Cycle Checkpoint Pathway Utilizing p53 and GADD45 is Defective in Ataxia–Telangiectasia," *Cell* 71(4):587–597, Nov. 13, 1992.
Keith et al., "PIK–related Kinases: DNA Repair, Recombination, and Cell Cycle Checkpoints," *Science* 270(5233):50–51, Oct. 6, 1995.

(Continued)

*Primary Examiner*—James Ketter
*Assistant Examiner*—David A. Lambertson
(74) *Attorney, Agent, or Firm*—Jane E. R. Potter; Young J. Suh; Alisa A. Harbin

(57) ABSTRACT

Inhibitors of KIAA0175 are provided that reduce the expression or biological activities of KIAA0175, p53 and/or p21 in a mammalian cell. KIAA0175 inhibitors include anti-sense molecules, ribozymes, antibodies and antibody fragments, proteins and polypeptides as well as small molecules. KIAA0175 inhibitors find use in compositions and methods for decreasing KIAA0175, p53 and/or p21 gene expression as well as methods for increasing the chemo and/or radiosensitivity of mammalian cells, including tumor cells, methods for decreasing the side effects of cancer therapy and methods for treating neoplastic diseases.

4 Claims, 1 Drawing Sheet

OTHER PUBLICATIONS

Kim et al., "Substrate Specificities and Identification of Putative Substrates of ATM Kinase Family Members," *J. Biol. Chem.* 274(53):37538–37543, Dec. 31, 1999.

Komarova et al., "Could p53 be a Target for Therapeutic Suppression?," *Semin. Cancer Biol.* 8(5):389–400, 1998.

Komarova et al., "Transgenic Mice with p53-Responsive lacZ: p53 Activity Varies Dramatically During Normal Development and Determines Radiation and Drug Sensitivity in vivo," *EMBO J.* 16(6):1391–1400, 1997.

Kubbutat et al., "Regulation of Mdm2-directed Degradation by the C Terminus of p53," *Molecular and Cellular Biology* 18(10):5690–5698, Oct. 1998.

Kubbutat et al., "Regulation of p53 Stability by Mdm2," *Nature* 387(6630):299–303, May 15, 1997.

Lehmann et al., "Miscellaneous Observations on DNA Repair in Ataxia–Telangiectasia," in Bridges and Harnden (eds.), *Ataxia–Telangiectasia—A Cellular and Molecular Link Between Cancer, Neurophathology and Immune Deficiency*, John Wiley and Sons, New York, 1982, pp. 347–353.

Lowe et al., "p53-Dependent Apoptosis Modulates the Cytotoxicity of Anticancer Agents," *Cell* 74(6):957–967, Sep. 24, 1993.

Lu et al., "Differential Induction of Transcriptionally Active p53 Following UV or Ionizing Radiation: Defects in Chromosome Instability Syndromes?," *Cell* 75(4):765–778, Nov. 19, 1993.

Matsuoka et al., "Linkage of ATM to Cell Cycle Regulation by the Chk2 Protein Kinase," *Science* 282(5395):1893–1897, Dec. 4, 1998.

Momand et al., "The mdm-2 Oncogene Product Forms a Complex with the p53 Protein and Inhibits p53-Mediated Transactivation," *Cell* 69(7):1237–1245, Jun. 26, 1992.

Nagase et al., "Prediction of the Coding Sequences of Unidentified Human Genes. V. The Coding Sequences of 40 New Genes (KIAA0161–KIAA0200) Deduced by Analysis of cDNA Clones from Human Cell Line KG–1," *DNA Research* 3(1):17–24, Feb. 29, 1996.

Oliner et al., "Oncoprotein MDM2 Conceals the Activation Domain of Tumour Suppressor p53," *Nature* 362(6423):857–860, Apr. 29, 1993.

Powis et al., "Wortmannin, a Potent and Selective Inhibitor of Phosphatidylinositol-3-Kinase," *Cancer Research* 54(9):2419–2423, May 1, 1994.

Price et al., "The Phosphatidylinositol 3-Kinase Inhibitor Wortmannin Sensitizes Murine Fibroblasts and Human Tumor Cells to Radiation and Blocks Induction of p53 Following DNA Damage," *Cancer Research* 56(2):246–250, Jan. 15, 1996.

Rogel et al., "p53 Cellular Tumor Antigen: Analysis of mRNA Levels in Normal Adult Tissues, Embryos, and Tumors," *Molecular and Cellular Biology* 5(10):2851–2855, Oct. 1985.

Rosenzweig et al., "Radiosensitization of Human Tumor Cells by the Phosphatidylinositol 3-Kinase Inhibitors Wortmannin and LY294002 Correlates with Inhibition of DNA-Dependent Protein Kinase and Prolonged G2-M Delay," *Clinical Cancer Research* 3(7):1149–1156, Jul. 1997.

Savitsky et al., "A Single Ataxia Telangiectasia Gene with a Product Similar to PI-3 Kinase," *Science* 268(5218):1749–1753, Jun. 23, 1995.

Sarkaria et al., "Inhibition of Phosphoinositide 3-Kinase Related Kinases by the Radiosensitizing Agent Wortmannin," *Cancer Research* 58(19):4375–4382, Oct. 1, 1998.

Schmid et al., "Expression of p53 During Mouse Embryogenesis," *Development* 113(3):857–865, Nov. 1991.

Schwartz et al., "Expression of p53 Protein in Spermatogenesis is Confined to the Tetraploid Pachytene Primary Spermatocytes," *Oncogene* 8(6):1487–1494, Jun. 1993.

Sherr, "Cancer Cell Cycles," *Science* 274(5293):1672–1677, Dec. 6, 1996.

Shieh et al., "DNA Damage–Induced Phosphorylation of p53 Alleviates Inhibition by MDM2," *Cell* 91(3):325–334, Oct. 31, 1997.

Siliciano et al., "DNA Damage Induces Phosphorylation of the Amino Terminus of p53," *Genes & Development* 11:3471–3481, 1997.

Tron et al., "p53-Regulated Apoptosis is Differentiation Dependent in Ultraviolet B–Irradiated Mouse Keratinocytes," *American J. of Pathology* 153(2):579–585, Aug. 1998.

Wang et al., "Loss of p21 Increases Sensitivity to Ionizing Radiation and Delays the Onset of Lymphoma in atm–Deficient Mice," *P.N.A.S. USA* 94:14590–14595, Dec. 1997.

Weinert et al., "The RAD9 Gene Controls the Cell Cycle Response to DNA, Damage in *Saccharomyces cerevisiae*," *Science* 241(4863):317–322, Jul. 15, 1988.

Westpahl et al., "atm and p53 Cooperate in Apoptosis and Suppression of Tumorigenesis, but not in Resistance to Acute Radiation Toxicity," *Nature Genetics* 16(4):397–401, Aug. 1997.

Wymann et al., "Wortmannin Inactivates Phosphoinositide 3-Kinase by Covalent Modification of Lys–802, a Residue Involved in the Phosphate Transfer Reaction," *Molecular and Cellular Biology* 16(4):1722–1733, Apr. 1996.

Nakashima et al., *Antisense Inhibition of Cyclin D1 in Human Head and Neck Squamous Cell Carcinoma*, Arch Otolaryngol Head Neck Surg, 126:957–961, 2000.

Monia et al., *Antitumor Activity of a Phosphorothioate Antisense Oligodeoxynucleotide Targeted Against C–raf Kinase*, Nature Medicine, 2(6):668–675, 1996.

Accession No. AA282064, 1997.

Heyer et al., *New Member of the Snf1/AMPK Kinase Family, Melk, Is Expressed in the Mouse Egg and Preimplantation Embryo*, Molecular Reproduction and Development, 47:2:148–156, 1997.

* cited by examiner

COMPOSITIONS AND METHODS FOR TREATING NEOPLASTIC DISEASE USING CHEMOTHERAPY AND RADIATION SENSITIZERS

CROSS-REFERENCE TO RELATED APPLICATIONS

This application claims priority from U.S. patent application Ser. No. 60/208,435 filed May 31, 2000, which is incorporated by reference herein in its entirety.

TECHNICAL FIELD

This invention relates generally to regulation of the cell cycle and cell death following exposure to agents that cause DNA damage. More specifically, the present invention provides compositions and methods for inhibiting KIAA0175 gene expression and/or biological activity as well as for reducing the expression and/or activation of p53, p21 or related proteins. Such compositions and methods are useful as chemotherapy and radiation sensitizers and, as a consequence, find utility in the treatment of neoplastic disease.

BACKGROUND OF THE INVENTION

Traditional chemo and radiotherapy for the treatment of tumors is limited in utility by the absence of target specificity. Methodologies employing targeted radiotherapy wherein radioisotopes are conjugated to tumor-seeking agents have been attempted to improve biological specificity. Unfortunately, very few selective agents are available for the many tumor types and where selective agents do exist, the therapeutic advantage has been minimal. Recent methodologies for treating neoplastic diseases attempt to improve specificity by employing a class of molecules called "sensitizers" that increase the sensitivity of treated cells to, for example, chemotherapy and γ-irradiation. For example, administration of drugs such as 5-fluorouracil and wortmannin has been attempted in order to increase cellular radiation sensitivity. Owing to the non-specific nature of these and other currently available "sensitizers," however, normal, non-neoplastic cells are subject to increased chemotherapy and radiation sensitivity thus resulting in a high level of cellular toxicity. What is urgently needed are chemotherapy and radiation sensitizers having improved specificity allowing preferential sensitivity of neoplastic as compared to normal cells. The KIAA0175 inhibitors of the present invention fulfill these and other related needs.

SUMMARY OF THE INVENTION

The present invention provides, in one embodiment, inhibitors of KIAA0175. Inventive inhibitors include, but are not limited to, anti-sense molecules, ribozymes, antibodies or antibody fragments, proteins or polypeptides as well as small molecules. Exemplary anti-sense molecules comprise at least 16, 17, 20 or 25 consecutive nucleotides of or hybridize under stringent conditions to the nucleic acid of SEQ ID NO:9. More preferred are anti-sense molecules that comprise at least 25 consecutive nucleotides of or hybridize under stringent conditions to the sequence of SEQ ID NO:9. Representative anti-sense molecules are provided herein as SEQ ID NO: 1, SEQ ID NO:3, and SEQ ID NO:5.

In further embodiments, compositions are provided that comprise one or more KIAA0175 inhibitor in a pharmaceutically acceptable carrier.

Additional embodiments provide methods of decreasing KIAA0175 gene expression or biological activity.

Still further embodiments provide methods for decreasing the expression of p53 and methods for decreasing the expression of p21.

Other embodiments provide methods of increasing the chemo and/or radiosensitivity of a mammalian cell, methods of reducing the side effects of cancer therapy and other types of stress associated with p53 induction and methods of treating neoplastic disease.

Each of the methods of the present invention have in common the administration of one or more inventive KIAA0175 inhibitor to a mammalian cell.

DETAILED DESCRIPTION OF THE INVENTION

Figure 1:
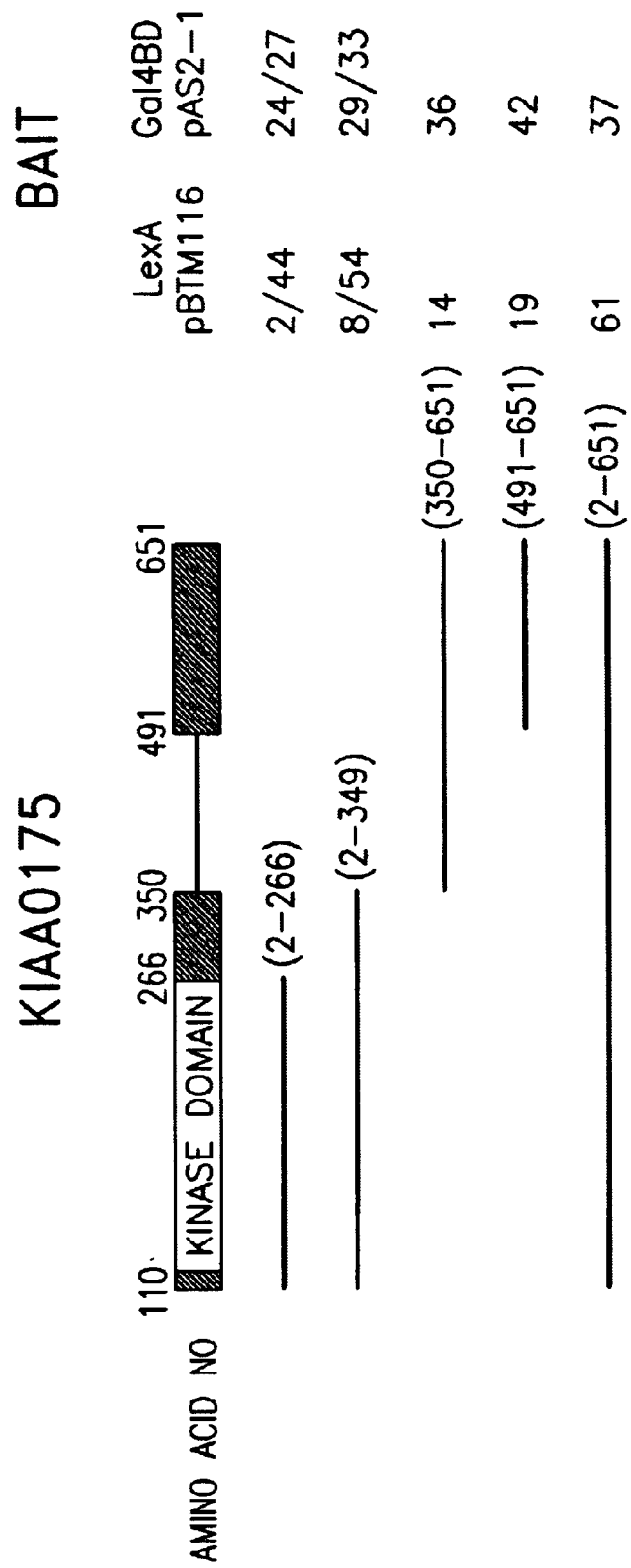
FIG. 1 is a diagram of various KIAA0175 two-hybrid bait constructs in the LexA plasmid vector pBTM116 and in the Gal4BD plasmid vector pAS2-1.

As noted above, the present invention is directed generally to regulation of the cell cycle and cell death following exposure to agents that cause DNA damage. More specifically, the invention disclosed herein provides inhibitors of KIAA0175, including anti-sense polynucleotides and ribozymes, proteins or polypeptides, antibodies or fragments thereof and small molecules; compositions comprising KIAA0175 inhibitors; methods of reducing p53 and/or p21 activation and/or or gene expression; methods of increasing the chemo and/or radiation sensitivity of a mammalian cell, methods of reducing the side effects of cancer therapy as well as methods of treating neoplastic disease. Each of these methods have in common the administration to a mammalian cell of one or more KIAA0175 inhibitor.

The p53 tumor suppressor is the most commonly mutated gene in human cancer. In normal cells under physiological conditions, p53 is expressed at low levels and has a short half-life. When cells are challenged by any of a variety of stress inducing stimuli, such as DNA damage, hypoxia, nucleotide deprivation, viral infection, oncogene activation, or factors that induce cell cycle arrest and cell death, p53 becomes stabilized and activated. Under such conditions, p53 acts as the "guardian of the genome" by facilitating genomic stability which is accomplished through the stalling of cellular growth and division at a variety of cell cycle checkpoints.

Eukaryotes from yeast to man have developed surveillance mechanisms that respond to DNA damage. In mammals, this surveillance mechanism includes a checkpoint, involving the ataxia telangiectasia mutated (ATM), p53 and p21 genes, that arrests cells in the G1 phase. For example, when cells are exposed to γ-irradiation, p53 becomes an active transcription factor that participates in the expression of various genes, including p21, that are important in regulating the cell cycle at the G1 to S phase checkpoint. El-Deiry, W. S. *Cancer Biology* 8:345–357 (1998); Cox, L. S. et al., *Bioessays* 17:501 (1995); Sherr, C. J., *Science* 274:1672 (1996).

Ataxia Telangiectasia (A-T) is an autosomal recessive disorder characterized by progressive cerebellar ataxia, neuronal degeneration, hypersensitivity to ionizing radiation (IR) and a high risk of cancer. Individuals afflicted with A-T exhibit acute sensitivity to ionizing radiation and radiomimetic chemicals, and their cell cycle checkpoints fail to be activated after treatment with these agents. Sadvitsky, K. et al., *Science* 268:1749 (1995). Thus, for example, when cell survival is used as an end-point, A-T fibroblasts and lymphoblasts are 3–4-fold more sensitive to ionizing radiation as compared to wild-type controls. Chen, P. C. et al., *Nature* 274:484–486 (1978) and Lehman, A. R. et al., In: "Ataxia-Telangiectasia—A Cellular and Molecular Link Between Cancer, Neuropathology and Immune Deficiency," pp. 347–353. (Ed. Bridges, B. A. and Harnden, D. G., Wiley, N.Y., 1982). Similarly, A-T cells are also hypersensitive to radiomimetic agents such as neocarcinostatin and bleomycin.

A-T is caused by a defect in the ATM gene the product of which has been implicated in both post-translational activation and increased expression of p53. Banin, et al., *Science* 281:1674–1677 (1998); Canman, et. al, *Science* 281:1677–1679 (1998). ATM has a phosphoinositide 3-kinase-related domain and a wortmannin-sensitive protein kinase activity, Keith, C. T. et al., *Science* 270:50 (1995), and phosphorylates p53 on a single amino acid residue, serine-15, in response to γ-irradiation. Cells from patients afflicted with A-T, resulting from an absence of ATM, show a reduced and delayed activation of p53 in response to DNA damage as evidenced by diminished p53 phosphorylation. Kastan, M. B. et al, *Cell* 71:587 (1992); Lu, X. et al., *Cell* 75:765 (1993); Siliciano, J. D. et al., *Genes Dev.* 11:3471 (1997) and Shieh, S.-Y. et al., *Cell* 91:325 (1997). Mutation of p53 at serine-15 reduces the ability of p53 to arrest cell growth. Fiscella, M. et al., *Oncogene* 8:1519 (1993).

In its normal, unphosphorylated state, p53 associates with the MDM2 protein which acts as a negative regulator of p53 stability by targeting it for proteolysis. Kubbutat, H. H. G. et al., *Nature* 387:299–303 (1997); Haupt, Y. et al., *Nature* 387:296–299 (1997); and Kubbutat, M. H. G. et al., *Mol. Cell. Biol.* 18:5690–5698 (1998). MDM2 binding also conceals p53's transactivation domain thereby blocking p53-dependent effects in cell cycle inhibition and apoptosis. Under conditions of cellular stress, such as challenge with γ-irradiation, phosphorylation at serine-15 reduces MDM2's p53 binding affinity preventing MDM2 mediated inhibition of p53-specific transcription as well as proteosome-mediated p53 degradation. It is for this reason that it has been suggested that p53 phosphorylation at serine-15 is important for genomic stability. Momand, J. et al., *Cell* 69:1237 (1992); Oliner, J. D., et al., *Nature* 362:857 (1993); Haupt, Y. et al., *Nature* 387:286 (1997); and Kubbutat, M. H. G. et al., *Nature* 387:299 (1997).

Arrest of the cell cycle at the G1 stage occurs, in part, through transcriptional activation of p21, a tight-binding inhibitor of Cdks that control entry into the S phase. Elledge, J. et al., *Trends Cell Biol.* 6:388 (1996). It has been shown that the absence of p21 activity increases cellular sensitivity to ionizing radiation and delays the onset of lymphoma in ATM-deficient mice. Wang, Y. A. et al., *Proc. Natl. Acad. Sci. U.S.A.* 94:14590–14595 (1997).

Checkpoint signal transduction was originally described in the yeast *Saccharomyces cerevisiae*. Weinert, T. A., et al., *Science* 241:317 (1988). Two genes, MEC1 and RAD53, are essential in the control of the yeast checkpoint. Mec1 is a member of the phosphatidyl inositol kinase superfamily and is believed to function as a protein kinase. Rad53 is a protein kinase that is phosphorylated and activated in response to DNA damage. Phosphorylation of Rad53 is dependent upon, inter alia, Mec1 indicating that Rad53 functions downstream of Mec1 to transduce the signal from DNA damage.

The true mammalian homologue to *Saccharomyces cerevisiae* Rad53 has been identified as the cell cycle regulatory protein Chk2 kinase. Matsuoka, S. et al., *Science* 282:1893–1897 (1998). As part of the present invention it was found that Rad53 is also homologous to a cDNA sequence first identified by Nagase, T. et al. and referred to as KIAA0175. *DNA Research* 3:17–24 (1996). These authors observed that KIAA0175 contains a region of homology with the family of serine-threonine protein kinases in particular the *Xenopus laevis* p69Eg3 protein kinase.

As disclosed herein, the KIAA0175 gene is expressed in a variety of tissues including testis, thymus, colon, placenta and spleen. KIAA0175 is also expressed in a number of cancer cell lines such as MOLT-4, HeLa, S3, K562, SW480, HL-60 and Raji cells. See Example 1 and FIGS. 1A–C.

The present invention also discloses that the protein product of the KIAA0175 gene possesses an autophosphorylation activity which activity depends upon, inter alia, a lysine residue at amino acid position 40. Thus, e.g., Cos7 cells transfected with a plasmid construct comprising an HA-tagged KIAA0175 wild-type or lysine to alanine substitution at position 40 (i.e., K40A) express the KIAA0175 protein but only the wild-type protein retains autophosphorylation activity as determined by the incorporation of $^{32}$P when immunoprecipitated protein is incubated in the presence of γ-$^{32}$P-ATP See Example 2. It is also observed that, following exposure of cells to either γ-irradiation or hydroxyurea, the levels of both endogenously expressed and recombinant KIAA0175 protein increase.

Radiation Sensitizers

Cells defective in ATM as well as in other members of the phosphatidylinositol-3-kinase (PI3K) family involved in regulating DNA damage dependent cell cycle checkpoints, such as ATR and DNA-PK, exhibit hypersensitivity to ionizing radiation and other DNA-damaging agents. It has been suggested that inhibitors of one or more of these kinases might enhance the cytotoxic effects of ionizing radiation or DNA-damaging cancer chemotherapeutic drugs by sensitizing cells to these agents. Sarkaria, J. N. et al., *Cancer Res.* 58:4375–4382 (1998) and Hosoi, Y. et al., *Int. J. Cancer* 78:642–647 (1998). This suggestion is supported by the observation that the sterol-like fungal metabolite, wortmannin, is an effective radiosensitizer. Chernikova, S. B. et al., *Rad. Res.* 151:159–166 (1999); Boulton, S. et al., *Carcinogenesis (Lond.)* 17:2285–2290 (1996); Price, B. D. et al., *Cancer Res.* 56:246–250 (1996); and Rosenzweig, K. E. et al., *Clin. Cancer Res.* 3:1149–1156 (1997). Wortmannin irreversibly inhibits the lipid kinase activities of mammalian PI-3Ks by covalent modification of a critical lysine residue in their phosphotransferase domains. Powis, G. et al., *Cancer Res.* 54:2419–2423 (1994) and Wymann, M. P. et al., *Mol. Cell. Biol.* 16:1722–1733 (1996).

Traditional radiosensitizers such as 5-fluorouracil either enhance the level of initial DNA damage caused by radiation or impede the repair of radiation-induced DNA lesions by inhibiting enzymes involved in DNA metabolism, synthesis and repair. Sarkaria, et al., supra. The intrinsic cytotoxicity associated with the administration of such drugs limits their clinical utility as radiation and chemotherapeutic agent sensitizers. Similarly, because wortmannin acts nonspecifically by inhibiting a broad range of PI3K related proteins, the risks associated with traditional radiosensitizers and chemosensitizers may also apply to the use of wortmannin. What is needed in the art are highly specific inhibitors of a DNA damage signaling pathway associated protein that is involved in cell cycle regulation. The present invention fulfills this need by providing specific inhibitors of KIAA0175 gene expression and/or biological activity. Such inhibitors abrogate cell cycle arrest and abolish the necessary damage repair, thus leaving cells vulnerable to the cytotoxicity of DNA damaging agents such as, e.g., ionizing radiation.

Inhibitors of KIAA0175 are Effective in Reducing KIAA0175, p53 and p21 Gene Expression The present invention provides inhibitors of KIAA0175. Inventive inhibitors include anti-sense molecules and ribozymes, proteins or polypeptides, antibodies or fragments thereof as well as small molecules. Each of these KIAA0175 inhibitors share the common feature that they reduce the expression and/or biological activity of KIAA0175 and, as a consequence, diminish the expression and/or activation of p53 and/or p21. In addition to the exemplary KIAA0175 inhibitors disclosed herein, alternative inhibitors may be obtained through routine experimentation utilizing methodology either specifically disclosed herein or as otherwise readily available to and within the expertise of the skilled artisan.

Anti-sense Molecules and Ribozymes

As discussed above, KIAA0175 inhibitors of the present invention include anti-sense molecules that, when administered to mammalian cells, are effective in reducing, for example, intracellular protein levels of p53 and/or p21. Anti-sense molecules bind in a sequence-specific manner to nucleic acids, such as mRNA or DNA. When bound to mRNA that has complementary sequences, anti-sense molecules prevent translation of the mRNA (see, e.g., U.S. Pat. No. 5,168,053 to Altman et al.; U.S. Pat. No. 5,190,931 to Inouye, U.S. Pat. No. 5,135,917 to Burch; U.S. Pat. No. 5,087,617 to Smith and Clusel et al. *Nucl. Acids Res.* 21:3405–3411 (1993), which describes dumbbell anti-sense oligonucleotides).

Anti-sense technology can be used to control gene expression through triple-helix formation, which promotes the ability of the double helix to open sufficiently for the binding of polymerases, transcription factors or regulatory molecules. See Gee et al., In Huber and Carr, "Molecular and Immunologic Approaches," Futura Publishing Co. (Mt. Kisco, N.Y.; 1994). Alternatively, an anti-sense molecule may be designed to hybridize with a control region of the KIAA0175 gene, e.g., promoter, enhancer or transcription initiation site, and block transcription of the gene; or block translation by inhibiting binding of a transcript to ribosomes. See generally, Hirashima et al. in *Molecular Biology of RNA: New Perspectives* (M. Inouye and B. S. Dudock, eds., 1987 Academic Press, San Diego, p. 401); *Oligonucleotides: Anti-sense Inhibitors of Gene Expression* (J. S. Cohen, ed., 1989 MacMillan Press, London); Stein and Cheng, *Science* 261:1004–1012 (1993); WO 95/10607; U.S. Pat. No. 5,359,051; WO 92/06693; and EP-A2-612844 each of which is incorporated herein by reference.

Briefly, such molecules are constructed such that they are complementary to, and able to form Watson-Crick base pairs with, a region of transcribed KIAA0175 mRNA sequence. The resultant double-stranded nucleic acid interferes with subsequent processing of the mRNA, thereby preventing protein synthesis.

In general, a portion of a sequence complementary to the KIAA0175 coding region may be used to modulate gene expression. The nucleic acid sequence of the human KIAA0175 cDNA is described in Nagase, T. et al., *DNA Research* 3:17–24 (1996), incorporated herein by reference, and is presented herein as SEQ ID NO:9. Alternatively, cDNA constructs that can be transcribed into anti-sense RNA may be introduced into cells or tissues to facilitate the production of anti-sense RNA. Thus, as used herein, the phrase "anti-sense molecules" broadly encompasses anti-sense oligonucleotides whether synthesized as DNA or RNA molecules as well as all plasmid constructs that, when introduced into a mammalian cell, promote the production of anti-sense RNA molecules. An anti-sense molecule may be used, as described herein, to inhibit expression of KIAA0175, p53 or p21 genes as well as any other gene that requires KIAA0175 for its expression.

Anti-sense molecules for use as described herein can be synthesized by any method known to those of skill in this art including chemical synthesis by, for example, solid phase phosphoramidite chemical synthesis. See, e.g., WO 93/01286; U.S. Pat. No. 6,043,090; U.S. Pat. No. 5,218,088; U.S. Pat. No. 5,175,269; and U.S. Pat. No. 5,109,124, each of which is incorporated herein by reference. Alternatively, RNA molecules may be generated by in vitro or in vivo transcription of DNA sequences encoding the KIAA0175 cDNA, or a portion thereof, provided that the DNA is incorporated into a vector downstream of a suitable RNA polymerase promoter (such as, e.g., T3, T7 or SP6). Large amounts of anti-sense RNA may be produced by incubating labeled nucleotides with a linearized KIAA0175 cDNA fragment downstream of such a promoter in the presence of the appropriate RNA polymerase. Such anti-sense molecules are preferably at least 16, 18 or 20 nucleotides in length as well as all intermediate lengths there between. More preferably, anti-sense molecules are at least 25 nucleotides in length. A further embodiment of the present invention provides anti-sense molecules that are at least 30, 40, 50, or 75 nucleotides in length, as well as all intermediate lengths there between. Within certain embodiments, an anti-sense molecule of the present invention will comprise a sequence that is unique to the KIAA0175 cDNA sequence of SEQ ID NO:9 or that can hybridize to the cDNA of SEQ ID NO:9 under conditions of high stringency. Within the context of the present invention, high stringency means standard hybridization conditions such as, e.g., 5×SSPE, 0.5% SDS at 65° C. or the equivalent thereof. See Sambrook et al., supra and *Molecular Biotechnology: Principles and Applications of Recombinant DNA*, supra incorporated herein by reference.

Anti-sense oligonucleotides are typically designed to resist degradation by endogenous nucleolytic enzymes by using such linkages as: phosphorothioate, methylphosphonate, sulfone, sulfate, ketyl, phosphorodithioate, phosphoramidate, phosphate esters, and other such linkages (see, e.g., Agrwal et al., *Tetrehedron Lett.* 28:3539–3542 (1987); Miller et al., *J. Am. Chem. Soc.* 93:6657–6665 (1971); Stec et al., *Tetrehedron Lett.* 26:2191–2194 (1985); Moody et al., *Nucl. Acids Res.* 12:4769–4782 (1989); Uznanski et al., *Nucl. Acids Res.* 17(12):4863–4871 (1989); Letsinger et al., *Tetrahedron* 40:137–143 (1984); Eckstein, *Annu. Rev. Biochem.* 54:367–402 (1985); Eckstein, *Trends Biol. Sci.* 14:97–100 (1989); Stein, in: *Oligodeoxynucleotides. Anti-sense Inhibitors of Gene Expression*, Cohen, Ed, Macmillan Press, London, pp. 97–117 (1989); Jager et al., *Biochemistry* 27:7237–7246 (1988)). Possible additional or alternative modifications include, but are not limited to, the addition of flanking sequences at the 5' and/or 3' ends and/or the inclusion of nontraditional bases such as inosine, queosine and wybutosine, as well as acetyl- methyl-, thio- and other modified forms of adenine, cytidine, guanine, thymine and uridine.

Within alternate embodiments of the present invention, KIAA0175 inhibitors may be ribozymes. A ribozyme is an RNA molecule that specifically cleaves RNA substrates, such as mRNA, resulting in specific inhibition or interference with cellular gene expression. As used herein, the term "ribozymes" includes RNA molecules that contain anti-sense sequences for specific recognition, and an RNA-cleaving enzymatic activity. The catalytic strand cleaves a specific site in a target RNA at greater than stoichiometric concentration.

A wide variety of ribozymes may be utilized within the context of the present invention, including for example, the hammerhead ribozyme (for example, as described by Forster and Symons, Cell 48:211–220 (1987); Haseloff and Gerlach, Nature 328:596–600 (1988); Walbot and Bruening, Nature 334:196 (1988); Haseloff and Gerlach, Nature 334:585 (1988)); the hairpin ribozyme (for example, as described by Haseloff et al., U.S. Pat. No. 5,254,678, issued Oct. 19, 1993 and Hempel et al., European Patent Publication No. 0 360 257, published Mar. 26, 1990); and Tetrahymena ribosomal RNA-based ribozymes (see Cech et al., U.S. Pat. No. 4,987,071). Ribozymes of the present invention typically consist of RNA, but may also be composed of DNA, nucleic acid analogs (e.g., phosphorothioates), or chimerics thereof (e.g., DNA/RNA/RNA).

Ribozymes can be targeted to any RNA transcript and can catalytically cleave such transcripts (see, e.g., U.S. Pat. No. 5,272,262; U.S. Pat. No. 5,144,019; and U.S. Pat. Nos. 5,168,053, 5,180,818, 5,116,742 and 5,093,246 to Cech et al.). According to certain embodiments of the invention, any such KIAA0175 mRNA-specific ribozyme, or a nucleic acid encoding such a ribozyme, may be delivered to a host cell to effect inhibition of KIAA0175 gene expression. Ribozymes and the like may therefore be delivered to the host cells by DNA encoding the ribozyme linked to a eukaryotic promoter, such as a eukaryotic viral promoter, such that upon introduction into the nucleus, the ribozyme will be directly transcribed.

Proteins and Polypeptides

In addition to the anti-sense molecules and ribozymes disclosed herein, supra, KIAA0175 inhibitors of the present invention also include proteins or polypeptides that are effective in either reducing KIAA0175 gene expression or in decreasing one or more of KIAA0175's biological activities. A variety of methods are readily available in the art by which the skilled artisan may, through routine experimentation, rapidly identify such KIAA0175 inhibitors. The present invention is not limited by the following exemplary methodologies.

As discussed above, KIAA0175 is an active protein kinase that possesses an autophosphorylation activity. Thus, inhibitors of KIAA0175's biological activities encompass those proteins and/or polypeptides that interfere with KIAA0175's kinase activity. Such interference may occur through direct interaction with KIAA0175's kinase domain or indirectly through non- or un-competitive inhibition such as via binding to an allosteric site. Accordingly, available methods for identifying proteins and/or polypeptides that bind to KIAA0175 may be employed to identify lead compounds that may, through the methodology disclosed herein, see infra, be characterized for their KIAA0175 inhibitory activity and/or efficacy as radiation sensitizers.

A vast body of literature is available to the skilled artisan that describes methods for detecting and analyzing protein-protein interactions. Reviewed in Phizicky, E. M. et al., Microbiological Reviews 59:94–123 (1995) incorporated herein by reference. Such methods include, but are not limited to physical methods such as, e.g., protein affinity chromatography, affinity blotting, immunoprecipitation and cross-linking as well as library-based methods such as, e.g., protein probing, phage display and two-hybrid screening. Other methods that may be employed to identify protein-protein interactions include genetic methods such as use of extragenic suppressors, synthetic lethal effects and unlinked noncomplementation. Exemplary methods are described in further detail below.

Inventive KIAA0175 inhibitors may be identified through biological screening assays that rely on the direct interaction between the KIAA0175 protein and a panel or library of potential inhibitor proteins. Biological screening methodologies, including the various "n-hybrid technologies," are described in, for example, Vidal, M. et al., Nucl. Acids Res. 27(4):919–929 (1999); Frederickson, R. M., Curr. Opin. Biotechnol. 9(1):90–6 (1998); Brachmann, R. K. et al., Curr. Opin. Biotechnol. 8(5):561–568 (1997); and White, M. A., Proc. Natl. Acad. Sci. U.S.A. 93:10001–10003 (1996) each of which is incorporated herein by reference.

The two-hybrid screening methodology may be employed to search new or existing target cDNA libraries for KIAA0175 binding proteins that have inhibitory properties. The two-hybrid system is a genetic method that detects protein-protein interactions by virtue of increases in transcription of reporter genes. The system relies on the fact that site-specific transcriptional activators have a DNA-binding domain and a transcriptional activation domain. The DNA-binding domain targets the activation domain to the specific genes to be expressed. Because of the modular nature of transcriptional activators, the DNA-binding domain may be severed covalently from the transcriptional activation domain without loss of activity of either domain. Furthermore, these two domains may be brought into juxtaposition by protein-protein contacts between two proteins unrelated to the transcriptional machinery. Thus, two hybrids are constructed to create a functional system. The first hybrid, i.e., the bait, consists of a transcriptional activator DNA-binding domain fused to a protein of interest. The second hybrid, the target, is created by the fusion of a transcriptional activation domain with a library of proteins or polypeptides. Interaction between the bait protein and a member of the target library results in the juxtaposition of the DNA-binding domain and the transcriptional activation domain and the consequent up-regulation of reporter gene expression.

A variety of two-hybrid based systems are available to the skilled artisan that most commonly employ either the yeast Gal4 or E. coli LexA DNA-binding domain (BD) and the yeast Gal4 or herpes simplex virus VP16 transcriptional activation domain. Chien, C.-T. et al., Proc. Natl. Acad. Sci. U.S.A. 88:9578–9582 (1991); Dalton, S. et al., Cell 68:597–612 (1992); Durfee, T. K. et al., Genes Dev. 7:555–569 (1993); Vojtek, A. B. et al., Cell 74:205–214 (1993); and Zervos, A. S. et al., Cell 72:223–232 (1993). Commonly used reporter genes include the E. coli lacZ gene as well as selectable yeast genes such as HIS3 and LEU2. Fields, S. et al., Nature (London) 340:245–246 (1989); Durfee, T. K., supra; and Zervos, A. S., supra. A wide variety of activation domain libraries are readily available in the art such that the screening for interacting proteins may be performed through routine experimentation.

Suitable bait proteins for the identification of KIAA0175 interacting proteins may be designed based on the KIAA0175 cDNA sequence presented herein as SEQ ID NO:9. Such bait proteins include either the full-length KIAA0175 protein or fragments thereof. For example, for screening of inhibitors that block KIAA0175's autophosphorylation activity, it may be advantageous to construct bait proteins that include lysine-40 and that encompass flanking amino acids thereto that comprise the protein's kinase domain. Exemplary KIAA0175 bait proteins, expressed as either LexA or Gal4BD, are depicted in FIG. 10. Representative bait constructs include the coding region for KIAA0175's kinase domain (e.g., the LexA constructs 2, 8 and 61 as well as the Gal4BD constructs 24, 29 and 37). In addition, LexA constructs 44 and 54 and Gal4BD constructs 27 and 33 each bear the single amino acid substitution within the kinase domain at K40A. FIG. 10 also depicts alternative bait constructs encoding KIAA0175 polypeptide fragments outside the kinase domain (e.g., the Lex A constructs 14 and 19 as well as the Gal4BD constructs 36 and 42).

Plasmid vectors, such as, e.g., pBTM116 and pAS2-1, for preparing KIAA0175 bait constructs and target libraries are readily available to the artisan and may be obtained from such commercial sources as, e.g., Clontech (Palo Alto, Calif.), Invitrogen (Carlsbad, Calif.) and Stratagene (La Jolla, Calif.). These plasmid vectors permit the in-frame fusion of cDNAs with the DNA-binding domains as LexA or Gal4BD, respectively.

KIAA0175 inhibitors of the present invention may alternatively be identified through one of the physical or biochemical methods available in the art for detecting protein-protein interactions.

Through the protein affinity chromatography methodology, lead compounds to be tested as potential KIAA0175 inhibitors may be identified by virtue of their specific retention to KIAA0175 when either covalently or non-covalently coupled to a solid matrix such as, e.g., Sepharose beads. The preparation of protein affinity columns is described in, for example, Beeckmans, S. et al., *Eur. J. Biochem.* 117:527–535 (1981) and Formosa, T. et al., *Methods Enzymol.* 208:24–45 (1991). Cell lysates containing the full complement of cellular proteins may be passed through the KIAA0175 affinity column. Proteins having a high affinity for KIAA0175 will be specifically retained under low-salt conditions while the majority of cellular proteins will pass through the column. Such high affinity proteins may be eluted from the immobilized KIAA0175 under conditions of high-salt, with chaotropic solvents or with sodium dodecyl sulfate (SDS). In some embodiments, it may be preferred to radiolabel the cells prior to preparing the lysate as an aid in identifying the KIAA0175 specific binding proteins. Methods for radiolabeling mammalian cells are well known in the art and are provided, e.g., in Sopta, M. et al., *J. Biol. Chem.* 260:10353–10360 (1985).

Suitable KIAA0175 proteins for affinity chromatography may be fused to a protein or polypeptide to permit rapid purification on an appropriate affinity resin. For example, the KIAA0175 cDNA may be fused to the coding region for glutathione S-transferase (GST) which facilitates the adsorption of fusion proteins to glutathione-agarose columns. Smith et al., *Gene* 67:31–40 (1988). Alternatively, fusion proteins may include protein A, which can be purified on columns bearing immunoglobulin G; oligohistidine-containing peptides, which can be purified on columns bearing $Ni^{2+}$; the maltose-binding protein, which can be purified on resins containing amylose; and dihydrofolate reductase, which can be purified on methotrexate columns. One exemplary tag suitable for the preparation of KIAA0175 fusion proteins that is presented herein is the epitope for the influenza virus hemagglutinin (HA) against which monoclonal antibodies are readily available and from which antibodies an affinity column may be prepared.

In those cases where candidate KIAA0175 inhibitors are directed against KIAA0175's kinase domain, it may be advantageous to phosphorylate the KIAA0175 protein prior to preparing the affinity column. As disclosed in Example 2, KIAA0175 may be phosphorylated when immobilized on a solid surface. Suitable phosphorylation conditions include 10 μM ATP, 1 mM DTT, 10 mM $MgCl_2$, 10 mM $MnCl_2$ and 50 mM Tris, pH 7.5.

Proteins that are specifically retained on a KIAA0175 affinity column may be identified after subjecting to SDS polyacrylamide gel electrophoresis (SDS-PAGE). Thus, where cells are radiolabeled prior to the preparation of cell lysates and passage through the KIAA0175 affinity column, proteins having high affinity for KIAA0175, may be detected by autoradiography. The identity of KIAA0175 specific binding proteins may be determined by protein sequencing techniques that are readily available to the skilled artisan, such as Mathews, C. K. et al., *Biochemistry*, The Benjamin/Cummings Publishing Company, Inc. pp.166–170 (1990).

Antibodies or Antibody Fragments

KIAA0175 inhibitors of the present invention include antibodies and/or antibody fragments that are effective in reducing KIAA0175 gene expression and/or biological activity. Suitable antibodies may be monoclonal, polyclonal or humanized monoclonal antibodies. Antibodies may be derived by conventional hybridoma based methodology, from antisera isolated from KIAA0175 inoculated animals or through recombinant DNA technology. Alternatively, inventive antibodies or antibody fragments may be identified in vitro by use of one or more of the readily available phage display libraries. Exemplary methods are disclosed herein.

In one embodiment of the present invention, KIAA0175 inhibitors are monoclonal antibodies that may be produced as follows. KIAA0175 protein may be produced, for example, by expression of KIAA0175 cDNA in a baculovirus based system. By this method, KIAA0175 cDNA or a fragment thereof is ligated into a suitable plasmid vector that is subsequently used to transfect Sf9 cells to facilitate protein production. In addition, it may be advantageous to incorporate an epitope tag or other moiety to facilitate affinity purification of the KIAA0175 protein. Clones of Sf9 cells expressing KIAA0175 are identified, e.g., by enzyme linked immunosorbant assay (ELISA), lysates are prepared and the KIAA0175 protein purified by affinity chromatography and the purified protein is injected, intraperitoneally, into BALB/c mice to induce antibody production. It may be advantageous to add an adjuvant, such as Freund's adjuvant, to increase the resulting immune response.

Serum is tested for the production of specific antibodies and spleen cells from animals having a positive specific antibody titer are used for cell fusions with myeloma cells to generate hybridoma clones. Supernatants derived from hybridoma clones are tested for the presence of monoclonal antibodies having specificity against KIAA0175. For a general description of monoclonal antibody methodology, See, e.g., Harlow and Lane, *Antibodies: A Laboratory Manual*, Cold Spring Harbor Laboratory (1988).

In addition to the baculovirus expression system, other suitable bacterial or yeast expression systems may be employed for the expression of KIAA0175 protein or polypeptides thereof. As with the baculovirus system, it may be advantageous to utilize one of the commercially available affinity tags to facilitate purification prior to inoculation of the animals. Thus, the KIAA0175 cDNA or fragment thereof may be isolated by, e.g., agarose gel purification and ligated in frame with a suitable tag protein such as 6-His, glutathione-S-transferase (GST) or other such readily available affinity tag. See, e.g., *Molecular Biotechnology: Prin-* ciples and Applications of Recombinant DNA, ASM Press pp. 160–161 (ed. Glick, B. R. and Pasternak, J. J. 1998).

In other embodiments of the present invention, KIAA0175 inhibitors are humanized anti-KIAA0175 monoclonal antibodies. The phrase "humanized antibody" refers to an antibody derived from a non-human antibody—typically a mouse monoclonal antibody. Alternatively, a humanized antibody may be derived from a chimeric antibody that retains or substantially retains the antigen-binding properties of the parental, non-human, antibody but which exhibits diminished immunogenicity as compared to the parental antibody when administered to humans. The phrase "chimeric antibody," as used herein, refers to an antibody containing sequence derived from two different antibodies (see, e.g., U.S. Pat. No. 4,816,567) which typically originate from different species. Most typically, chimeric antibodies comprise human and murine antibody fragments, generally human constant and mouse variable regions.

Because humanized antibodies are far less immunogenic in humans than the parental mouse monoclonal antibodies, they can be used for the treatment of humans with far less risk of anaphylaxis. Thus, these antibodies may be preferred in therapeutic applications that involve in vivo administration to a human such as, e.g., use as radiation sensitizers for the treatment of neoplastic disease or use in methods to reduce the side effects of, e.g., cancer therapy.

Humanized antibodies may be achieved by a variety of methods including, for example: (1) grafting the non-human complementarity determining regions (CDRs) onto a human framework and constant region (a process referred to in the art as "humanizing"), or, alternatively, (2) transplanting the entire non-human variable domains, but "cloaking" them with a human-like surface by replacement of surface residues (a process referred to in the art as "veneering"). In the present invention, humanized antibodies will include both "humanized" and "veneered" antibodies. These methods are disclosed in, e.g., Jones et al., *Nature* 321:522–525 (1986); Morrison et al., *Proc. Natl. Acad. Sci., U.S.A.*, 81:6851–6855 (1984); Morrison and Oi, *Adv. Immunol.*, 44:65–92 (1988); Verhoeyer et al., Science 239:1534–1536 (1988); Padlan, *Molec. Immun.* 28:489–498 (1991); Padlan, *Molec. Immunol.* 31(3):169–217 (1994); and Kettleborough, C. A. et al., *Protein Eng.* 4(7):773–83 (1991) each of which is incorporated herein by reference.

The phrase "complementarity determining region" refers to amino acid sequences which together define the binding affinity and specificity of the natural Fv region of a native immunoglobulin binding site. See, e.g., Chothia et al., *J. Mol. Biol.* 196:901–917 (1987); Kabat et al., U.S. Dept. of Health and Human Services NIH Publication No. 91-3242 (1991). The phrase "constant region" refers to the portion of the antibody molecule that confers effector functions. In the present invention, mouse constant regions are substituted by human constant regions. The constant regions of the subject humanized antibodies are derived from human immunoglobulins. The heavy chain constant region can be selected from any of the five isotypes: alpha, delta, epsilon, gamma or mu.

One method of humanizing antibodies comprises aligning the non-human heavy and light chain sequences to human heavy and light chain sequences, selecting and replacing the non-human framework with a human framework based on such alignment, molecular modeling to predict the conformation of the humanized sequence and comparing to the conformation of the parent antibody. This process is followed by repeated back mutation of residues in the CDR region which disturb the structure of the CDRs until the predicted conformation of the humanized sequence model closely approximates the conformation of the non-human CDRs of the parent non-human antibody. Such humanized antibodies may be further derivatized to facilitate uptake and clearance, e.g., via Ashwell receptors. See, e.g., U.S. Pat. Nos. 5,530,101 and 5,585,089 which patents are incorporated herein by reference.

It will be appreciated that alternative KIAA0175 inhibitor antibodies may be readily obtained by other methods commonly known in the art. One exemplary methodology for identifying antibodies having a high specificity for KIAA0175 is the phage display technology.

Phage display libraries for the production of high-affinity antibodies are described in, for example, Hoogenboom, H. R. et al., *Immunotechnology* 4(1):1–20 (1998); Hoogenboom, H. R., *Trends Biotechnol.* 15:62–70 (1997) and McGuinness, B. et al., *Nature Bio. Technol.* 14:1149–1154 (1996) each of which is incorporated herein by reference. Among the advantages of the phage display technology is the ability to isolate antibodies of human origin that cannot otherwise be easily isolated by conventional hybridoma technology. Furthermore, phage display antibodies may be isolated in vitro without relying on an animal's immune system.

Antibody phage display libraries may be accomplished, for example, by the method of McCafferty et al., *Nature* 348:552–554 (1990) which is incorporated herein by reference. In short, the coding sequence of the antibody variable region is fused to the amino terminus of a phage minor coat protein (pIII). Expression of the antibody variable region-pIII fusion construct results in the antibody's "display" on the phage surface with the corresponding genetic material encompassed within the phage particle.

KIAA0175 protein suitable for screening a phage library may be obtained by, for example, expression in baculovirus Sf9 cells as described, supra. Alternatively, the KIAA0175 coding region may be PCR amplified using primers specific to the desired region of the KIAA0175 protein. For example, where the inhibitor is directed against KIAA0175's kinase domain, fragments may be amplified that encode the amino acid sequence flanking lysine 40 in the active site. Exemplary PCR primers for the amplification of KIAA0175 include, but are not limited to, those set forth in SEQ ID NOs:7 and 8. As discussed above, the KIAA0175 protein may be expressed in *E. coli* or yeast as a fusion with one of the commercially available affinity tags.

The resulting fusion protein may then be adsorbed to a solid matrix, e.g., a tissue culture plate or bead. Phage expressing antibodies having the desired anti-KIAA0175 binding properties may subsequently be isolated by successive panning, in the case of a solid matrix, or by affinity adsorption to a KIAA0175 antigen column. Phage having the desired KIAA0175 inhibitory activities may be reintroduced into bacteria by infection and propagated by standard methods known to those skilled in the art. See Hoogenboom, H. R., *Trends Biotechnol.*, supra for a review of methods for screening for positive antibody-pIII phage.

Small Molecules

The present invention also provides small molecule KIAA0175 inhibitors that may be readily identified through routine application of high-throughput screening (HTS) methodologies. Reviewed by Persidis, A., *Nature Biotechnology* 16:488–489 (1998). HTS methods generally refer to those technologies that permit the rapid assaying of lead compounds, such as small molecules, for therapeutic potential. HTS methodology employs robotic handling of test materials, detection of positive signals and interpretation of data. Such methodologies include, e.g., robotic screening technology using soluble molecules as well as cell-based systems such as the two-hybrid system described in detail above.

A variety of cell line-based HTS methods are available that benefit from their ease of manipulation and clinical relevance of interactions that occur within a cellular context as opposed to in solution. Lead compounds may be identified via incorporation of radioactivity or through optical assays that rely on absorbance, fluorescence or luminescence as read-outs. See, e.g., Gonzalez, J. E. et al., *Curr. Opin. Biotechnol.* 9(6:624–631 (1998) incorporated herein by reference.

HTS methodology may be employed, e.g., to screen for lead compounds that block one of KIAA0175's biological activities such as its autophosphorylation activity. By this method, KIAA0175 protein may be immunoprecipitated from cells expressing the protein and applied to wells on an assay plate suitable for robotic screening. Individual test compounds may then be contacted with the immunoprecipitated protein and the effect of each test compound on KIAA0175 kinase activity assessed by, e.g., incubating in the presence of $\gamma$-$^{32}$P-ATP in a suitable buffer system, see Example 2, and measuring the incorporation of $^{32}$P.

Methods for Assessing the Efficacy of KIAA0175 Inhibitors

Lead molecules or compounds, whether anti-sense molecules or ribozymes, proteins and/or peptides, antibodies and/or antibody fragments or small molecules, that are identified either by one of the methods described herein or via techniques that are otherwise available in the art, may be further characterized in a variety of in vitro, ex vivo and in vivo animal model assay systems for their ability to inhibit KIAA0175 gene expression or biological activity. As discussed in further detail in the Examples provided below, KIAA0175 inhibitors of the present invention are effective in reducing not only KIAA0175 expression levels but also, inter alia, (1) in decreasing intracellular p53 and/or p21 protein levels in the target mammalian cell; (2) in reducing cell cycle phase transitions; and (3) in increasing cells to chemotherapy and/or radiation sensitizers. Thus, the present invention further discloses methods that permit the skilled artisan to assess the effect of candidate inhibitors on each of these three parameters.

As noted above and as presented in the Examples provided herein, supra, candidate KIAA0175 inhibitors may be tested by administration to cells that either express endogenous KIAA0175 or that are made to express KIAA0175 by transfection of a mammalian cell with a recombinant KIAA0175 plasmid construct. Suitable cell lines for this purpose include, e.g., the HT1080 and HCT116 cell lines both of which express relatively high levels of endogenous KIAA0175. While the utility of these cell lines is specifically disclosed herein, it will be apparent to one of skill in the art that alternative cell lines may be used in accordance with the methodologies disclosed herein the choice of which cell line will depend, for example, on the specific application contemplated.

Effective KIAA0175 inhibitory molecules will be effective in reducing the levels of KIAA0175 mRNA as determined, e.g., by Northern blot or RT-PCR analysis. See Example 4, for a general description of these procedures, see, e.g., Sambrook et al., *Molecular Cloning: A Laboratory Manual* Cold Spring Harbor Press (1989) and *Molecular Biotechnology: Principles and Applications of Recombinant DNA*, ASM Press (ed. Glick, B. R. and Pasternak, J. J. 1998) incorporated herein by reference. The effectiveness of a given candidate anti-sense molecule may be assessed by comparison with a control "anti-sense" molecule known to have no substantial effect on KIAA0175 expression when administered to a mammalian cell. Exemplary control molecules include the AKT and FITC primers disclosed in Example 4.

Putative KIAA0175 inhibitory anti-sense molecules may be additionally characterized for their effect on p53 and p21 protein levels when administered to a mammalian cell. Thus, for example, such candidate molecules may be administered to HT1080 or HCT116 cells. Following a suitable period of culture, the transfected cells may additionally be challenged with $\gamma$-irradiation. The cellular protein levels of p53 and p21 may be assessed either before irradiation or at various time-points after challenge, e.g., by Western analysis using antibodies having specificity to each of these proteins. See Examples 5 and 6 and, e.g., Sambrook et al., supra. Levels of a suitable negative control protein, such as Erk2, may be analyzed in order to verify the specificity of each candidate KIAA0175 inhibitory anti-sense molecule. Effective KIAA0175 inhibitory anti-sense molecules may cause a reduction in either or both of p53 and p21 protein levels. As well, KIAA0175 inhibitory anti-sense molecules used as radiation sensitizers, see infra, will also reduce the $\gamma$-irradiation induced increase in p53 and/or p21 protein levels.

In alternate embodiments of the present invention, the effect of KIAA0175 inhibitors on the rate of DNA synthesis after challenge with a radiation or chemotherapeutic agent may be assessed by, e.g., the method of Young and Painter. *Hum. Genet.* 82:113–117 (1989). Briefly, culture cells may be incubated in the presence of $^{14}$C-thymidine prior to exposure to, e.g., X-rays. Immediatedly after irradiation, cells are incubated for a short period prior to addition of $^{3}$H-thymidine. Cells are washed, treated with perchloric acid and filtered (Whatman GF/C). The filters are rinsed with perchloric acid, 70% alcohol and then 100% ethanol; radioactivity is measured and the resulting $^{3}$H/$^{14}$C ratios used to determine the rates of DNA synthesis.

KIAA0175 inhibitors effective in reducing KIAA0175 gene expression and/or p21 or p53 protein levels by one or more of the methods discussed above may be further characterized in vivo for efficacy in one of the readily available animal model systems. The various animal model systems for study of cancer and genetic instability associated genes have been the subject of a recent review. Donehower, L. A. *Cancer Surveys* 29:329–352 (1997) incorporated herein by reference.

By still further embodiments, KIAA0175 inhibitors may be identified by assessing the effect of candidate inhibitors on cell cycle arrest in response to $\gamma$-irradiation as disclosed herein, infra, in Example 7.

KIAA0175 Inhibitors as Chemotherapy and Radiation Sensitizers

As discussed above, the present invention provides KIAA0175 inhibitors as well as compositions and methods employing KIAA0175 inhibitors that are useful as chemotherapy and radiation sensitizers for, inter alia, the treatment of neoplastic disease. As used herein, the term "sensitizer" generally refers to the property of a molecule or composition to induce in a cell hypersensitivity to a chemotherapeutic drug, to ionizing radiation and/or to other DNA-damaging agents. Exemplary methods employ gene delivery techniques, as described in detail, infra, to administer KIAA0175 inhibitory anti-sense molecules to target cells. See, also, Example 8.

The methods provided herein share the common feature that hypersensitization is achieved by administration of one or more KIAA0175 inhibitors. Within some embodiments, chemotherapy and/or radiation hypersensitivity is achieved by administration of an anti-sense molecule. In certain other embodiments, chemotherapy and/or radiosensitizing anti-sense molecules may be linked to a radiation-inducible promoter to localize expression by external radiation beams. See, e.g., McBride, W. H. et al., *Nat. Med.* 1:1215–1217 (1995) and Weichselbaum, R. R. et al., *Cancer Res.* 54:4266–4269 (1994) (describing the combination of gene delivery and radiation as a paradigm for radiotherapy). By alternate embodiments, expression of the KIAA0175 inhibitory anti-sense molecule may be restricted by use of a tissue-specific or cell cycle-specific promoter. Vile, R. G. et al., *Cancer Res.* 53:962–967 (1993) and Vile, R. G., *Semin. Cancer Biol.* 5:437–443 (1994) (discussing tumor specific targeted gene expression). Other embodiments of the present invention employ trophic viruses that are confined to particular organs or structures. Each of these exemplary methods is incorporated herein by reference.

By the present methods, beneficial improvement of chemo and/or radiotherapy will be achieved despite low transfection efficiency and/or transient gene expression. This will be the case especially where the gene-delivery methodology is repeated throughout the course of therapy. Transfection efficiencies are expected to be in the order of 10% to 70%.

Use of KIAA0175 Inhibitors to Reduce the Severity of Cancer Therapy Side Effects Conventional cancer treatment regimens, including both chemotherapy and radiation therapy, frequently have severe side effects that compromise their efficacy. These side effects result, in part, from p53-mediated apoptosis of treated cells. Thus, it has been suggested that suppression of p53 activity may be effective in reducing apoptosis and as a consequence decreasing the adverse side effects associated with cancer therapy. Komarov, P. G. et al., *Science* 285:1733–1737 (1999) incorporated herein by reference.

High levels of p53 have been detected in a variety of normal tissues, including lymphoid and hematopoietic organs, intestinal epithelia, and the testis that are damaged by anticancer treatments. Rogel, A. et al., *Mol. Cell. Biol.* 5:2851 (1985); Schmidt, P. et al., *Development* 113:857 (1991); Schwartz, D. et al., *Oncogene* 8:1487 (1993) and Komarova, E. A. et al., *EMBO J.* 16:1391 (1997). In addition, p53-dependent apoptosis occurs in these sensitive tissues shortly after γ-irradiation. Komarova, id.; Hendry, J. H. et al., *Int. J. Radiat. Biol.* 70:677 (1996); and Tron, V. A. et al., *Am. J. Pathol.* 153:579 (1998). Thus, it has been proposed that p53 may be an appropriate target for therapeutic suppression thereby reducing damage to normal cells. Komarova, B. A. et al., *Semin. Cancer Biol.* 8:389 (1998).

It has been discovered, as part of the present invention, that KIAA0175 inhibitors are effective in reducing the intracellular levels of p53 protein. Accordingly, KIAA0175 inhibitors may be effective as drugs for reducing the side effects of cancer therapy and other types of stress associated with p53 induction.

Lead compounds may be identified, by the methods provided herein or by other suitable methods available in the art, that are effective in reducing p53 protein levels when administered to a mammalian cell. For example, as disclosed in Example 5, KIAA0175 inhibitors may be administered to HT1080 or HCT116 cells and the resulting levels of p53 may be assessed by Western analysis using p53-specific antibodies. KIAA0175 inhibitors may be effective in reducing p53 expression levels may be further tested, by the method of Komarov, P. G. et al., supra, in a conventional model of p53-dependent apoptosis such as the mouse cell line C8. Lowe, S. W. et al., *Cell* 74:957 (1993) incorporated herein by reference (describing the C8 cell-line as a mouse embryo fibroblast transformed with E1a+ras that undergoes rapid p53-dependent apoptosis in response to a variety of treatments).

The in vivo efficacy of KIAA0175 inhibitors found to be active in reducing p53-mediated cellular apoptosis may be further characterized in a suitable animal model system. For example, two different strains of mice, i.e., C57BL or Balb/c, may be treated with lethal and sublethal doses of whole-body γ-irradiation after administration of one or more KIAA0175 inhibitor. See Komarov, P. G. et al., supra.

Administration of KIAA0175 Inhibitors and Compositions Thereof

The present invention provides KIAA0175 inhibitors and compositions comprising one or more KIAA0175 inhibitor as well as methods that employ these inventive inhibitors in in vivo, ex vivo, and in vitro applications where it is advantageous to reduce or eliminate the expression or activity of KIAA0175 or a functionally downstream molecule such as p53 or p21. As indicated above, KIAA0175 inhibitor based compositions will find utility in the treatment of neoplastic disease and related conditions where treatment regimens are improved by radiation hypersensitivity of tumor cells. Alternatively, KIAA0175 inhibitors may find use as drugs for reducing the side effects of, e.g., cancer therapeutics and other agents that cause p53-mediated cell stress and apoptosis.

Compositions may be administered parenterally, topically, orally or locally for therapeutic treatment. Preferably, the compositions are administered orally or parenterally, i.e., intravenously, intraperitoneally, intradermally or intramuscularly.

Inventive compositions will include one or more KIAA0175 inhibitor and may further comprise a pharmaceutically acceptable carrier or excipient. A variety of aqueous carriers may be used, e.g., water, buffered water, 0.4% saline, 0.3% glycine and the like, and may include other proteins for enhanced stability, such as albumin, lipoprotein, globulin, etc., subjected to mild chemical modifications or the like.

Inhibitors of the present invention may be combined with additional or alternative inhibitors of, for example, ATM, DNA-PK or ATR to achieve still greater levels of radiation hypersensitivity. See, e.g., Westpahl et al., *Nat. Genet.* 16:397 (1997) incorporated herein by reference.

KIAA0175 inhibitors useful as radiation sensitizers or otherwise useful in the treatment of disease in mammals will often be prepared substantially free of other naturally occurring immunoglobulins or other biological molecules. Preferred KIAA0175 inhibitors will also exhibit minimal toxicity when administered to a mammal.

The compositions of the invention may be sterilized by conventional, well known sterilization techniques. The resulting solutions may be packaged for use or filtered under aseptic conditions and lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride and stabilizers (e.g., 1–20% maltose, etc.).

The selection of the appropriate method for administering KIAA0175 inhibitors of the present invention will depend on the nature of the application envisioned as well as the nature of the KIAA0175 inhibitor. Thus, for example, the precise methodology for administering a KIAA0175 inhibitor will depend upon whether it is an anti-sense molecule, a protein and/or peptide, an antibody or antibody fragment or a small molecule. Other considerations include, for example, whether the KIAA0175 inhibitor will be used to increase radiation hypersensitivity or to reduce the side effects of cancer therapeutics.

A variety of methods are available in the art for the administration of anti-sense molecules. Exemplary methods include gene delivery techniques, including both viral and non-viral based methods as well as liposome mediated delivery methods.

Gene delivery methodologies will be effective to, for example, sensitize tumor cells to irradiation and/or chemotherapeutic drugs. See, Wheldon, T. E. et al., *Radiother Oncol* 48(1):5–13 (1998) (gene delivery methodologies for enhancement of fractionated radiotherapy). By these methodologies, substantial therapeutic benefit may be achieved despite transfection efficiencies significantly less than 100%, transient retention of the transfected inhibitor and/or existence of a subpopulation of target cells refractory to therapy.

As discussed above, the limitation of conventional radiotherapy is that its tumor specificity is weak. This limitation may be overcome by direct targeting of the expression of anti-sense KIAA0175 inhibitors to tumor cells. This may be achieved, for example, by linking the KIAA0175 inhibitor gene to a radiation-inducible promoter so that gene therapy can be localized by external radiation beams. McBride, W. H. et al., *Nat. Med.* 1:1215–1217 (1995) and Weichselbaum, R. R. et al., *Lancet Suppl* II:S10–S12 (1997) each of which is incorporated herein by reference.

Alternatively, gene delivery methodology may be used to directly knock-out endogenous KIAA0175 within tumor cells thereby rendering the tumor cells hypersensitive to radiation and chemotherapeutic drugs. For example, the KIAA0175 gene may be targeted by transfection of a gene delivery vector carrying a KIAA0175 inhibitor. Preferential transfection into or expression within tumor cells may be achieved through use of a tissue-specific or cell cycle-specific promoter, such as, e.g., promoters for prostate-specific antigen or for immunoglobulin genes (Vile, R. G. et al., *Cancer Res.* 53:962–967 (1993) and Vile, R. G., *Semin. Cancer Biol.* 5:437–443 (1994)) or through the use of trophic viruses that are confined to particular organs or structures, such as, e.g., a replication selective and neurotrophic virus that can only infect proliferating cells in the central nervous system.

Thus, to achieve therapeutic benefit, KIAA0175 within the tumor cells should be preferentially inhibited. This can be accomplished by transfecting a gene expressing a KIAA0175 inhibitor, a KIAA0175 anti-sense molecule, a KIAA0175 gene specific repressor, or an inhibitor of the protein product of the KIAA0175 gene.

As used herein, the phrase "gene delivery vector" refers generally to a nucleic acid construct that carries and, within certain embodiments, is capable of directing the expression of an anti-sense molecule of interest, as described in, for example, *Molecular Biotechnology: Principles and Applications of Recombinant DNA*, Ch. 21, pp.555–590 (ed. B. P. Glick and J. J. Pasternak, 2$^{nd}$ ed. 1998); Jolly, *Cancer Gene Ther.* 1:51–64 (1994); Kimura, *Human Gene Ther.* 5:845–852 (1994); Connelly, *Human Gene Ther.* 6:185–193 (1995); and Kaplitt, *Nat. Gen.* 6:148–153 (1994).

A number of virus and non-virus based gene delivery vector systems have been described that are suitable for the administration of KIAA0175 inhibitors. Virus based gene delivery systems include, but are not limited to retrovirus, such as Moloney murine leukemia virus, spumaviruses and lentiviruses; adenovirus; adeno-associated virus; and herpes-simplex virus vector systems. Viruses of each type are readily available from depositories or collections such as the American Type Culture Collection (ATCC; 10801 University Boulevard, Manassas, Va. 20110-2209) or may be isolated from known sources using commonly available materials and techniques.

The gene delivery vector systems of the present invention will find applications both in in vivo as well as ex vivo therapeutic regimens. Each of these applications is described in further detail below.

1. Retroviral Gene Delivery Vector Systems

Within one aspect of the present invention, retroviral gene delivery vectors are provided that are constructed to carry or express a KIAA0175 inhibitory anti-sense molecule. As used herein, the term "KIAA0175 inhibitory anti-sense molecule" refers generally to a nucleic acid sequence having KIAA0175 inhibitory activity. More specifically, such anti-sense molecules will reduce KIAA0175 gene expression as well as p53 and/or p21 protein levels. Retroviral gene delivery vectors of the present invention may be readily constructed from a wide variety of retroviruses, including for example, B, C, and D type retroviruses as well as spumaviruses and lentiviruses. See *RNA Tumor Viruses*, Cold Spring Harbor Laboratory (2$^{nd}$ ed. 1985).

Any of the above retroviruses may be readily utilized in order to assemble or construct retroviral gene delivery vectors given the disclosure provided herein, and standard recombinant DNA techniques. See, e.g., Sambrook et al, *Molecular Cloning: A Laboratory Manual*, Cold Spring Harbor Laboratory Press (2d ed. 1989) and Kunkle, *Proc. Natl. Acad. Sci. U.S.A.* 82:488 (1985). In addition, within certain embodiments of the invention, portions of the retroviral gene delivery vectors may be derived from different retroviruses.

A retroviral vector, suitable for the expression of a KIAA0175 inhibitory anti-sense molecule, must include at least one transcriptional promoter/enhancer or locus defining element(s), or other elements that control gene expression by other means such as alternate splicing, nuclear RNA export, post-translational modification of messenger, or post-transcriptional modification of protein. Such vector constructs must also include a packaging signal, long terminal repeats (LTRs) or portion thereof, and positive and negative strand primer binding sites appropriate to the retrovirus used (if these are not already present in the retroviral vector). Optionally, the retroviral vector may also include a signal that directs polyadenylation, selectable markers such as Neomycin resistance, TK, hygromycin resistance, phleomycin resistance histidinol resistance, or DHFR, as well as one or more restriction sites and a translation termination sequence. Within one aspect of the present invention, retroviral gene delivery vector constructs are provided comprising a 5' LTR, a tRNA binding site, a packaging signal, one or more heterologous sequences, an origin of second strand DNA synthesis and a 3' LTR, wherein the vector construct lacks gag/pol or env coding sequences.

Other retroviral gene delivery vectors may likewise be utilized within the context of the present invention, including, for example, those disclosed in the following each of which is incorporated herein by reference: EP 0,415,731; WO 90/07936; WO 94/03622; WO 93/25698; WO 93/25234; U.S. Pat. No. 5,219,740; WO 93/11230; WO 93/10218; Vile et al., *Cancer Res.* 53:3860–3864 (1993); Vile et al., *Cancer Res.* 53:962–967 (1993); Ram et al., *Cancer Res.* 53:83–88 (1993); Takamiya et al., *J. Neurosci. Res.* 33:493–503 (1992); Baba et al., *J. Neurosurg.* 79:729–735 (1993); U.S. Pat. No. 4,777,127, GB 2,200,651, EP 0,345,242 and WO 91/02805.

Packaging cell lines suitable for use with the above described retroviral gene delivery vector constructs may be readily prepared. See, e.g., U.S. Pat. Nos. 5,716,832 and 5,591,624. These packaging cell lines may be utilized to create producer cell lines (also termed vector cell lines or "VCLs") for the production of recombinant vector particles. It may be preferred to use packaging cell lines made from human (e.g., HT1080 cells) or mink parent cell lines, thereby allowing production of recombinant retroviruses that avoid inactivation in human serum.

2. Adeno-Associated Viral Gene Delivery Vector Systems

Adeno-associated viruses (AAV) possess a number of qualities that make them particularly suitable for the development of gene delivery vectors generally and for the delivery of polynucleotides encoding KIAA0175 inhibitory anti-sense molecules in particular. For a general review of AAV expression systems, see Rabinowitz et al., *Current Opin. Biotech.* 9(5):470–475 (1998). AAV is a non-pathogenic, defective human parvovirus that is non-infective without an adeno or herpes helper virus. Thus, in the absence of a helper virus, AAV becomes integrated latently into the host genome. In addition, AAV has the advantage over the retroviruses, discussed above, in being able to transduce a wide range of both dividing and quiescent cell types.

A variety of AAV gene delivery vectors may be utilized to direct the expression of one or more KIAA0175 inhibitor anti-sense molecule. Representative examples of such vectors include the AAV vectors disclosed by Srivastava in WO 93/09239; Samulski, et al. *J. Virol.* 63:3822–3828 (1989); Mendelson, et al. *Virol.* 166:154–165 (1988); and Flotte, et al. *Proc. Natl. Acad. Sci. USA.* 90(22):10613–10617 (1993) incorporated herein by reference.

Briefly, an AAV gene delivery vector of the present invention may include, in order, a 5'-associated virus inverted terminal repeat; a polynucleotide encoding the KIAA0175 inhibitory anti-sense molecule; a sequence operably linked to the KIAA0175 inhibitory anti-sense molecule that regulates its expression in a target tissue, organ or cell; and a 3'-associated virus inverted terminal repeat. A suitable regulatory sequence for the expression of KIAA0175 inhibitory anti-sense molecule is, e.g., the enhancer/promoter sequence of cytomegalovirus (CMV). In addition, the AAV vector may preferably have a polyadenylation sequence such as the bovine growth hormone (BGH) polyadenylation sequence. Generally, AAV vectors should have one copy of the AAV ITR at each end of the KIAA0175 inhibitory anti-sense molecule, to allow replication, packaging, efficient integration into the host cell genome and rescue from the chromosome. The 5' ITR sequence consists of nucleotides 1 to 145 at the 5' end of the AAV DNA genome, and the 3' ITR includes nucleotides 4681 to 4536 of the AAV genome. Preferably, the AAV vector may also include at least 10 nucleotides following the end of the ITR (i.e., a portion of the so-called "D region").

Optimal packaging of an adeno-associated virus gene delivery vector requires that the 5' and 3' ITRs be separated by approximately 2–5 kb. It will be apparent, however, that the ideal spacing between ITR sequences may vary depending on the particular packaging system utilized. This spacing may be achieved by incorporating a "stuffer" or "filler" polynucleotide fragment to bring the total size of the nucleic acid sequence between the two ITRs to between 2 and 5 kb. Thus, where the KIAA0175 inhibitory anti-sense molecule is smaller than 2–5 kb, a non-coding stuffer polynucleotide may be incorporated, for example, 3' to the 5' ITR sequence and 5' of the KIAA0175 inhibitory anti-sense molecule. The precise nucleotide sequence of the stuffer fragment is not an essential element of the final construct.

Depending upon the precise application contemplated, rather than incorporating a stuffer fragment, multiple copies of the KIAA0175 inhibitory anti-sense molecule may be inserted, inter alia, to achieve the optimal ITR sequence spacing. It may be preferred to organize the polynucleotides as two or more separate transcription units each with its own promoter and polyadenylation signal.

Recombinant AAV vectors of the present invention may be generated from a variety of adeno-associated viruses, including for example, serotypes 1 through 6. For example, ITRs from any AAV serotype are expected to have similar structures and functions with regard to replication, integration, excision and transcriptional mechanisms.

Within certain embodiments of the invention, expression of the KIAA0175 inhibitory anti-sense molecule may be accomplished by a separate promoter (e.g., a viral promoter). Representative examples of suitable promoters in this regard include a CMV promoter, an RSV promoter, an SV40 promoter, or a MoMLV promoter. Other promoters that may similarly be utilized within the context of the present invention include cell or tissue specific promoters or inducible promoters. Representative inducible promoters include tetracycline-response promoters (e.g., the "Tet" promoter) as described in Gossen et al., *Proc. Natl. Acad. Sci. U.S.A.* 89:5547–5551 (1992); Gossen et al., *Science* 268:1766–1769 (1995); Baron et al., *Nucl. Acids Res.* 25:2723–2729 (1997); Blau et al., *Proc. Natl. Acad. Sci. U.S.A.* 96:797–799 (1999); Bohl et al., *Blood* 92:1512–1517 (1998); and Haberman et al., *Gene Therapy* 5: 1604–1611 (1998); the ecdysone promoter system as described in No et al., *Proc. Natl. Acad. Sci. U.S.A.* 93:3346–3351 (1996); and other regulated promoters or promoter systems as described in Rivera et al., *Nat. Med.* 2:1028–1032 (1996).

The AAV gene delivery vector may also contain additional sequences, for example from an adenovirus, which assist in effecting a desired function for the vector. Such sequences include, for example, those which assist in packaging the AAV gene delivery vector in adenovirus particles.

Packaging cell lines suitable for producing adeno-associated viral vectors may be routinely prepared given readily available techniques. See, e.g., U.S. Pat. No. 5,872,005, incorporated herein by reference. At a minimum, suitable packaging systems for AAV gene delivery systems of the present invention will include the AAV replication and capsid genes.

Preferred packaging cell lines may contain both an AAV helper virus as well as an AAV gene delivery vector containing the KIAA0175 inhibitory anti-sense molecule. For detailed descriptions of representative packaging cell line systems, see, e.g. Holscher, C. et al., *J. Virol.* 68:7169–7177 (1994); Clark, K. R et al., *Hum. Gene Ther.* 6:1329–1341 (1995); and Tamayosa, K. et al., *Hum. Gen. Ther.* 7:507–513 (1996) which are incorporated herein by reference.

Alternatively, packaging of AAV may be achieved in vitro in a cell free system to obviate transfection protocols or packaging cell lines. Such in vitro systems incorporate an AAV gene delivery vector bearing the KIAA0175 inhibitory anti-sense molecule and a source of Rep-protein, capsid-protein and Adenovirus proteins that supply helper-viral functions. The latter proteins are typically supplied in the form of a cell extract. Representative in vitro systems are further described in Ding, L. et al., *Gen. Ther.* 4:1167–1172 (1997) and Zhou, Z. et al., *J. Virol.* 72:3241–3247 (1998) which are incorporated herein by reference.

3. Other Viral Gene Delivery Vector Systems

In addition to retroviral vectors and adeno-associated virus-based vectors, numerous other viral gene delivery vector systems may also be utilized for the expression of KIAA0175 inhibitory anti-sense molecules. For example, within one embodiment of the invention adenoviral vectors may be employed. Representative examples of such vectors include those described by, for example, Berkner, *Biotechniques* 6:616–627 (1988); Rosenfeld et al., *Science* 252:431–434 (1991); WO 93/9191; Kolls et al., *Proc. Natl. Acad. Sci. U.S.A.* 91(1):215–219 (1994); Kass-Eisler et al., *Proc. Natl. Acad. Sci. USA.* 90(24):11498–502 (1993); Guzman et al., *Circulation* 88(6):2838–48 (1993); Guzman et al., *Cir. Res.* 73(6):1202–1207 Zabner et al., *Cell* 75(2:207–216 (1993); Li et al., *Hum. Gene Ther.* 4(4): 403–409 (1993); Caillaud et al., *Eur. J. Neurosci.* 5(10): 1287–1291 (1993); Vincent et al., *Nat. Genet.* 5(2):130–134 (1993); Jaffe et al., *Nat. Genet.* 1(5):372–378 (1992); and Levrero et al., *Gene* 101(2):195–202 (1991); and WO 93/07283; WO 93/06223; and WO 93/07282.

Gene delivery vectors of the present invention also include herpes vectors. Representative examples of such vectors include those disclosed by Kit in *Adv. Exp. Med. Biol.* 215:219–236 (1989); and those disclosed in U.S. Pat. No. 5,288,641 and EP 0176170 (Roizman). Additional exemplary herpes simplex virus vectors include HFEM/ICP6-LacZ disclosed in WO 95/04139 (Wistar Institute), pHSVlac described in Geller, *Science* 241:1667–1669 (1988), and in WO 90/09441 and WO 92/07945; HSV Us3::pgC-lacZ described in Fink, *Human Gene Therapy* 3:11–19 (1992); and HSV 7134, 2 RH 105 and GAL4 described in EP 0453242 (Breakefield), and those deposited with the ATCC as accession numbers ATCC VR-977 and ATCC VR-260.

Gene delivery vectors may also be generated from a wide variety of other viruses including, for example, poliovirus (Evans et al., *Nature* 339:385–388 (1989); and Sabin, *J. Biol. Standardization* 1:115–118 (1973)); rhinovirus; pox viruses, such as canary pox virus or vaccinia virus (Fisher-Hoch et al., *Proc. Natl. Acad. Sci. U.S.A.* 86:317–321 (1989); Flexner et al., *Ann. N.Y. Acad. Sci.* 569:86–103 (1989); Flexner et al., *Vaccine* 8:17–21 (1990); U.S. Pat Nos. 4,603,112, 4,769,330 and 5,017,487; WO 89/01973); SV40 (Mulligan et al., *Nature* 277:108–114 (1979); influenza virus (Luytjes et al., *Cell* 59:1107–1113 (1989); McMicheal et al., *N. Eng. J. Med.* 309:13–17 (1983); and Yap et al., *Nature* 273:238–239 (1978)); HIV (Poznansky, *J. Virol.* 65:532–536 (1991)); measles (EP 0 440,219); astrovirus (Munroe et al., *J. Vir.* 67:3611–3614 (1993)); and coronavirus, as well as other viral systems (e.g., EP 0,440,219; WO 92/06693; U.S. Pat. No. 5,166,057).

4. Non-Viral Gene Delivery Vectors

Other gene delivery vectors and methods that may be employed for the expression of KIAA0175 inhibitory anti-sense molecules such as, for example, nucleic acid expression vectors; polycationic condensed DNA linked or unlinked to killed adenovirus alone, for example, see Curiel, *Hum Gene Ther* 3:147–154 (1992); ligand linked DNA, for example, see Wu, *J Biol Chem* 264:16985–16987 (1989); eucaryotic cell delivery vectors; deposition of photopolymerized hydrogel materials; hand-held gene delivery particle gun, as described in U.S. Pat. No. 5,149,655; ionizing radiation as described in U.S. Pat. No. 5,206,152 and in WO 92/11033; nucleic charge neutralization or fusion with cell membranes. Additional approaches are described in Philip, *Mol Cell Biol* 14:2411–2418 (1994), and in Woffendin, *Proc. Natl. Acad. Sci.* 91:1581–1585 (1994).

Particle mediated gene delivery may be employed. Briefly, the KIAA0175 inhibitory anti-sense molecule of interest can be inserted into conventional vectors that contain conventional control sequences for high level expression, and then be incubated with synthetic gene delivery molecules such as polymeric DNA-binding cations like polylysine, protamine, and albumin, linked to cell targeting ligands such as asialoorosomucoid, as described in Wu, et al., *J. Biol. Chem.* 262:4429–4432 (1987), insulin as described in Hucked, *Biochem Pharmacol* 40:253–263 (1990), galactose as described in Plank, *Bioconjugate Chem* 3:533–539 (1992), lactose or transferrin.

Naked DNA may also be employed. Exemplary naked DNA introduction methods are described in WO 90/11092 and U.S. Pat. No. 5,580,859. Uptake efficiency may be improved using biodegradable latex beads. DNA coated latex beads are efficiently transported into cells after endocytosis initiation by the beads. The method may be improved further by treatment of the beads to increase hydrophobicity and thereby facilitate disruption of the endosome and release of the DNA into the cytoplasm.

Liposomes that can act as gene delivery vehicles are described in U.S. Pat. No. 5,422,120, PCT Patent Publication Nos. WO 95/13796, WO 94/23697, and WO 91/144445, and European Patent Publication No. 524,968. Nucleic acid sequences can be inserted into conventional vectors that contain conventional control sequences for high level expression, and then be incubated with synthetic gene delivery molecules such as polymeric DNA-binding cations like polylysine, protamine, and albumin, linked to cell targeting ligands such as asialoorosomucoid, insulin, galactose, lactose, or transferrin. Other delivery systems include the use of liposomes to encapsulate DNA comprising the gene under the control of a variety of tissue-specific or ubiquitously-active promoters. Further non-viral delivery suitable for use includes mechanical delivery systems such as the approach described in Woffendin et al., *Proc. Natl. Acad. Sci. U.S.A.* 91(24):11581–11585 (1994). Moreover, the coding sequence and the product of expression of such can be delivered through deposition of photopolymerized hydrogel materials.

Exemplary liposome and polycationic gene delivery vehicles are those described in U.S. Pat. Nos. 5,422,120 and 4,762,915, in PCT Patent Publication Nos. WO 95/13796, WO 94/23697, and WO 91/14445, in European Patent Publication No. 524,968 and in Starrier, *Biochemistry*, pp. 236–240 (1975) W. H. Freeman, San Francisco; Shokai, *Biochem. Biophys. Acta.* 600:1 (1980); Bayer, *Biochem. Biophys. Acta.* 550:464 (1979); Rivet, *Methods Enzymol.* 149:119 (1987); Wang, *Proc. Natl. Acad. Sci. U.S.A.* 84:7851 (1987); Plant, *Anal. Biochem.* 176:420 (1989).

"Therapeutically effective amount" as used herein, is the precise amount of the compositions of the present invention to be administered and can be determined by a physician with consideration of individual differences in age, weight, tumor type and size, or extent of metastasis, and condition of the patient. It can generally be stated that a pharmaceutical composition comprising the subject inhibitors is therapeutically effective when any effect of the inhibitors described herein is achieved (e.g. inhibition of KIAA0175 expression levels, of p53, p21, or other molecules downstream of KIAA0175), when the desired sensitization of tumor cells to irradiation or to chemotherapeutic drugs is achieved, and/or when the side effects of cancer therapeutics are reduced. The optimal dosage and treatment regime for a particular patient can readily be determined by one skilled in the art of medicine by monitoring the patient for signs of disease or improvement and adjusting the treatment accordingly.

EXAMPLES

The following experimental examples are offered by way of illustration, not limitation.

Example 1

Expression of KIAA0175 mRNA

This example discloses Northern blot analysis of the tissue- and cancer cell-specific expression of KIAA0175 mRNA.

A KIAA0175 specific DNA probe was generated from a 0.7 kb internal fragment of the KIAA0175 open reading frame. This DNA fragment was radiolabeled with $\alpha$-$^{32}$P-ATP by standard methods (Stratagene; La Jolla, Calif.) and was used to probe commercially available tissue- and cancer cell-line blots obtained from Clontech (7760-1, 7759-1, and 7757-1). Specific hybridization of the KIAA0175 probe was detected by autoradiography.

Of the various tissues tested by Northern blot analysis, testis expressed the highest level of KIAA0175 mRNA. Thymus and colon expressed a lower level of KIAA0175 mRNA followed, in order of decreasing expression, by placenta and spleen. Of the various cancer cell lines examined, MOLT-4 showed the highest levels of KIAA0175 mRNA followed by HeLa S3, K562, and SW480 cells, that expressed intermediate levels of KIAA0175 mRNA, and HL-60 and Raji cells that expressed still lower levels of KIAA0175 mRNA. KIAA0175 mRNA in A549 and G361 cells was barely detectable.

Example 2

Autophosphorylation of the KIAA0175 Protein

This example discloses that KIAA0175 possesses an autophosphorylation activity and that this activity may be eliminated by a single amino acid substitution at lysine-40.

Plasmid constructs expressing the KIAA0175 wild-type and the kinase inactive K40A mutant protein were prepared. These plasmids express both KIAA0175 variants as hemagglutinin (HA) fusion proteins thereby facilitating their isolation via immunoprecipitation and detection through Western hybridization.

The plasmid vector pcDNA3.1 (Invitrogen) contains a multiple cloning site and CMV promoter to facilitate the subcloning and expression the KIAA0175 cDNAs having an HA tag sequence.

Cos 7 cells were transfected with either the naked vector pcDNA3.1 or the pcDNA3.1 expressing the wild-type or kinase inactive KIAA0175 proteins. The KIAA0175 proteins were immunoprecipitated with anti-HA monoclonal antibody (COVANCE/Babco). Kinase activity was determined by incubating the immunoprecipitated proteins in the presence of 10 $\mu$Ci $\gamma$-$^{32}$P-ATP, 10 mM ATP, 1 mM DTT, 10 mM MgCl$_2$, 10 mM MnCl$_2$ and 50 mM Tris, pH7.5. Proteins were subjected to electrophoresis on an SDS polyacrylamide gel and the proteins were transferred to a nitrocellulose membrane. Kinase activity was determined by measuring $^{32}$P incorporation as detected by autoradiography. Immunoprecipitated protein was detected by Western analysis with anti-HA antibodies.

The data revealed that Cos 7 cells transfected with the naked pcDNA3.1 plasmid vector do not produce HA precipitable KIAA0175 protein. Cos 7 cells transfected with either the wild-type or the K40A mutant produce approximately equivalent amounts of the respective KIAA0175 protein but only the wild-type protein has significant kinase activity.

Example 3

Recombinant and Endogenous KIAA0175 Protein Levels After Exposure of Cells to $\gamma$-irradiation and Hydroxyurea This Example discloses that KIAA0175 protein levels increase following exposure of cells expressing either recombinant or endogenous KIAA0175 to $\gamma$-irradiation or hydroxyurea.

Recombinant HA-KIAA0175 protein levels in Cos 7 cells were detected either without treatment or after treatment with either $\gamma$-irradiation or hydroxyurea. Lysates were loaded directly onto SDS polyacrylamide gels without prior immunoprecipitation of the HA fusion proteins. The HA-fusion proteins were detected by probing with anti-HA antibodies.

Similarly, endogenous KIAA0175 protein levels in cells were detected either without treatment or after treatment with either $\gamma$-irradiation (HeLa cells) or hydroxyurea (Arent cells). Lysates were loaded directly onto SDS polyacrylamide gels without prior immunoprecipitation of the KIAA0175 proteins. The KIAA0175 proteins were detected by probing with anti-KIAA0175 antibodies.

In total, the data revealed that treatment of Cos 7 cells with $\gamma$-irradiation or hydroxyurea caused an increase in KIAA0175 protein levels whether the KIAA0175 protein was expressed as a recombinant HA-fusion protein or was endogenously expressed.

Example 4

Kinetics of KIAA0175 Transcript Following Administration of an Anti-sense Oligonucleotide This example discloses that KIAA0175 mRNA levels may be downregulated by administration of a KIAA0175 anti-sense oligonucleotide.

The following anti-sense oligonucleotides were used in the experiments disclosed herein:

```
KIA175-545 (SEQ ID NO:1): 5'-GAGGTCCCTGTGAGCATAGCCCTGG-3'
RC545      (SEQ ID NO:2): 5'-GGTCCCGATACGAGTGTCCCTGGAG-3'

KIA175-736 (SEQ ID NO:3): 5'-TGCCCATGCTCCAAACATCTGCCTC-3'
RC736      (SEQ ID NO:4): 5'-CTCCGTCTACAAACCTCGTACCCGT-3'
```

-continued

```
KIA175-1182 (SEQ ID NO:5): 5'-GGGTAGCACTGGCTTGTCCACAGGA-3'
RC1182 (SEQ ID NO:6): 5'-AGGACACCTGTTCGGTCACGATGGG-3'

FITC (SEQ ID NO:11): 5'-TCTGCTGCTGTCGACAACGAGTGTC-3'
AKT 1-1548 (SEQ ID NO:12): 5'-CCATAGTGAGGTTGCATCTGGTGCC-3'
```

HT 1080 cells express endogenous KIAA0175. These cells were transfected with either the FITC (negative control) or AKT1 (positive control) oligonucleotides), 1182, or 545 oligonucleotides. Briefly, 100 nM of the respective anti-sense oligonucleotide was mixed with lipitoid 1 transfection reagent (Huang et al., *Chemistry and Biology* 5(6):346–354 (1998)) in a 1:3 volume to volume ratio in OPTI-MEM (GibcoBRL). The mixture was added to the HT1080 cells in complete medium (EMEM, 10% heat inactivated fetal bovine serum (FBS), 2 mM L-Glutamine, 100 U/ml Penicillin, and 1000 µg/ml Streptomycin) and the cells were incubated at 37° C. for ~4–5 hours in the presence of the anti-sense oligonucleotides before changing to fresh complete medium. Total RNA was extracted at day 1 or 24, 48, or 72 hours following transfection and mRNA levels of KIAA0175 were detected by Northern analysis. 20 µg of total RNA were subjected to electrophoresis on a denaturing agarose gel. RNA was transferred to nitrocellulose and KIAA0175 mRNA was detected by probing with a $^{32}$P-labeled, 0.7 kb KIAA0175 cDNA fragment. To control for equal loading of individual lanes, the blot was stripped of the KIAA0175 probe and re-probed with a $^{32}$P-labeled G3PDH cDNA probe obtained from Clontech.

The data showed that any of the KIAA0175 anti-sense oligonucleotides tested, i.e., 1182, 545 or 736, were effective in reducing the level of KIAA0175 mRNA expression. In contrast, reverse control primers (RC1182 and RC736) as well as the control primers AKT and FITC were all ineffective in reducing KIAA0175 mRNA expression. KIAA0175 mRNA expression increased gradually over the time range of 24 to 72 hours after 545 and 1182 anti-sense oligonucleotide administration. FITC had no effect on KIAA0175 mRNA expression over the time range tested.

Example 5

Western Analysis of KIAA0175, P53, ERK2 and P21 Protein Levels Following Administration of an Anti-sense Oligonucleotide This example discloses the effect of KIAA0175 anti-sense oligonucleotide administration on KIAA0175, p53 and p21 protein levels.

In separate experiments, either HT1080 or HCT116 cells expressing endogenous KIAA0175 and p53 were transfected with either FITC, KIAA0175 anti-sense oligonucleotides (i.e. 545 or 1182), or the corresponding reverse control oligonucleotides (RC or RC545). Total cell lysates were fractionated by SDS-polyacrylamide gel electrophoresis and transferred to nitrocellulose membranes. Specific proteins were detected by Western analysis using antibodies to either KIAA0175 (rabbit polyclonal antisera), p53, Erk2, or p21 antibodies as indicated. Antibodies against p53, p21 and Erk2 were obtained from Santa Cruz Biotechnology, Inc. (Santa Cruz, Calif.).

In HT1080 cells, the administration of either of the KIAA0175 anti-sense oligonucleotides caused a reduction in both p53 and p21 protein levels but did not affect Erk2 protein level. Maximal 1182 anti-sense activity in HT1080 cells was observed at 48 hrs for both KIAA0175 and p53 proteins. Similar results were obtained with HCT116 cells, disclosed herein, further suggesting the general nature of the effect of KIAA0175 anti-sense across a variety of cell lines.

Example 6

Western Analysis of P53, ERK2 and P21 Protein Levels Following γ-Irradiation of Cells Transfected with a KIAA0175 Anti-Sense Oligonucleotide This example discloses the effect of a KIAA0175 antisense oligonucleotide on γ-irradiation-induced up-regulation of p53 and p21 protein levels.

HT1080 cells expressing endogenous KIAA0175 were transfected with the KIAA0175 anti-sense oligonucleotide (1182) and the corresponding reverse control oligonucleotide (RC1182). After culture for 24-hours, the transfected cells were treated with 10 Gy of γ-irradiation. At various times after irradiation, cells were harvested and lysates prepared and subjected to SDS-PAGE. p53, Erk2, and p21 proteins were detected by Western analysis.

The data showed that administration of anti-sense oligonucleotide 1182 blocked the γ-irradiation induced increase in p53 protein level observed with the RC1182 oligonucleotide. Similarly, the 1182 oligonucleotide caused a reduction of p21 protein levels. As a consequence of decreased p53 expression levels, cells transfected with, e.g., the 1182 anti-sense oligonucleotide exhibit an increase in radiation sensitivity and, thus, the 1182 anti-sense oligonucleotide functions as a radiation sensitizer.

Example 7

Partial Loss of Cell Cycle Arrest Upon γ-Irradiation in KIAA0175 Anti-sense Molecule Transfected HT1080 Cells This Example discloses the effect of KIAA0175 anti-sense molecules on cell-cycle arrest in response to γ-irradiation.

Because both p53 and p21 are involved in the G1 to S phase cell cycle transition, the following experiments were performed in order to assess the effect of KIAA0175 anti-sense molecules on cell cycle regulation.

Table 1 discloses the percentage of HT1080 cells in each stage of the cell cycle at various times following exposure to γ-irradiation. By 24 hours, cells were arrested in both the G1 and G2 phases as evidenced by the elevated percentage of cells in G0/G1 and G2/M phases as compared to the diminished percentage of cells in the S phase.

TABLE 1

|  | 0 | 24 | 50 | 72 hr after γ-IR (8Gy) |
| --- | --- | --- | --- | --- |
| G0-G1 | 50.5 | 59.7 | 65.2 | 67.6 |
| S | 35.6 | 13.6 | 9.5 | 10.5 |
| G2-M | 13.9 | 26.7 | 25.3 | 21.9 |

Table 2 discloses the effect of KIAA0175 anti-sense molecules on γ-irradiation induced cell-cycle arrest. In cells transfected with anti-sense molecules, there was a reduction in the accumulation of cells in the G1 phase and a minimized reduction in the number of cells in the S phase as compared to cells transfected with a "reverse-control" anti-sense molecule as control. In contrast, the percentage of cells present in the G2/M phase transition was unaffected by the administration of a KIAA0175 anti-sense molecule thus demonstrating that the effect of KIAA0175 anti-sense molecules in relieving the γ-irradiation induced cell-cycle arrest is specific for the G1 phase in HT1080 cells.

TABLE 2

|       | RC1182 |      | 1182 |       |
|-------|--------|------|------|-------|
|       | −      | +    | −    | +     |
| G0-G1 | 47.6   | 52.5 | 47.4 | 39.3  |
| S     | 33     | 14.9 | 25.7 | 18.6  |
| G2-M  | 19.4   | 32.6 | 26.8 | 42.17 |

Without being limited to a specific theory of the present invention, these data are supportive of the essential role played by p53 in DNA-damage cell-cycle arrest at the G1 checkpoint and suggest that the administration of KIAA0175 anti-sense molecules causes a decrease in p53 gene expression and activity thereby alleviating the γ-irradiation induced block in the G1-S cell-cycle transition.

Example 8

Sensitization of HCT-116 Cells to γ-Irradiation and Hydroxyurea by Administration of KIAA0175 Anti-Sense Molecules This Example discloses that KIAA0175 anti-sense molecules are effective in sensitizing cells to both γ-irradiation and hydroxyurea.

γ-irradiation treatment was performed as follows: On day one, HCT116 cells were transfected with either the KIAA0175 anti-sense molecule No. 545 (545) or with the 545 reverse control molecule (RC) and plated onto tissue-culture plates. On day three, one plate each of 545 and RC transfected cells were treated with γ-irradiation (2, 4 or 8 Gy) and cultured an additional 2 hours. The γ-irradiation treated cells as well as untreated control HCT116 cells were trypsinized, counted and seeded in triplicate onto 6-well tissue culture plates to a density of 1000 cells per well. After 11 days of culture, the cells were assayed for viability by staining with Crystal Violet. Total numbers of cell colonies were then counted. Representative data showed that administration of the 545 anti-sense molecule increased the sensitivity of HCT116 cells to γ-irradiation, as evidenced by a decrease in the number of viable colonies arising from 545-treated cells as compared to RC-treated cells.

Hydroxyurea treatment was performed as follows: On day one, HCT116 cells were transfected with either the KIAA0175 anti-sense molecule No. 545 (545) or with the 545 reverse control molecule (RC) and plated onto tissue-culture plates. The following day (day two), one plate each of 545 and RC transfected cells were treated with hydroxyurea (1 mM final concentration) and cultured an additional 24 hours. On day three, the hydroxyurea treated cells as well as untreated control HCT116 cells were trypsinized, counted and seeded in triplicate onto 6-well tissue culture plates to a density of 1000 cells per well. After 11 days of culture, the cells were assayed for viability by staining with Crystal Violet. Total numbers of cell colonies were then counted. Representative data showed that administration of the 545 anti-sense molecule increased the sensitivity of HCT116 cells to hydroxyurea, as evidenced by a decrease in the number of viable colonies arising from 545-treated cells as compared to RC-treated cells.

Example 9

Sensitization of Tumor Cells to Chemotherapeutic Drugs by Administration of KIAA0175 Anti-Sense Oligonucleotides This example discloses the sensitization of tumor cells by administration of KIAA0175 anti-sense molecules.

The effect of KIAA0175 anti-sense molecules on cell sensitivity to chemotherapeutic drugs was tested on several cell lines using the lactate dehydrogenase (LDH) cytotoxicity assay essentially as follows:

Day 1: Cells were seeded in 4 separate 96 well plates, typically 5000 cells/well and incubated at 37° C. and 5% $CO_2$.

Day 2: Cells were transfected with the KIA175-1182 and KIA175-545 anti-sense oligonucleotides (SEQ ID NOs:5 and 1, respectively) as well as the reverse complement controls, RC1182 and RC545 (SEQ ID NOs:6 and 2, respectively) essentially as described in Example 4, with and without drug. One plate (day 0) was left untransfected as a seeding control.

The transfection was carried out using a lipid vehicle for delivery as described in WO 01/16306, hereby incorporated in its entirety. Briefly, the transfection used agents known as "lipitoids" and "cholesteroids", described, for example, in PCT publications WO 01/16306, WO 98/06437 and WO 99/08711, based on U.S. Ser. No. 60/023,867, 60/054,743, and 09/132,808, which are also hereby incorporated by reference. These lipid-cationic peptoid conjugates are shown in these references to be effective reagents for the delivery of plasmid DNA to cells in vitro. Any of the carriers described in the above-referenced applications are suitable for use in transfection of the oligonucleotides described herein.

These compounds may be prepared by conventional solution or solid-phase synthesis. In one such procedure, as described in WO 99/08711, cited above, the N-terminus of a resin-bound peptoid is acylated with a spacer such as Fmocaminohexanoic acid or Fmoc-3-alanine. After removal of the Fmoc group, the primary amino group is reacted with cholesterol chloroformate to form a carbamate linkage. The product is then cleaved from the resin with trifluoroacetic acid and purified by reverse-phase HPLC. A fatty acid-derived lipid moiety, such as a phospholipid, may be used in place of the steroid moiety. The steroid or other lipid moiety may also be linked to the peptoid moiety by other linkages, of any effective length, readily available to the skilled practitioner.

Depending on the cell type, different lipid vehicles were used for different lengths of time for transfection. However, the transfection time did not exceed 24 hrs. The transfection was carried out in complete medium and the final anti-sense oligonucleotide concentration was 300 nM per well. In the wells with drug, the drug was added to the culture at the beginning of the transfection.

Starting on Day 3: Cells were recovered, 1 plate/day and release of LDH into the supernatant was measured using a kit from Roche according to manufacturer's instructions (Roche Diagnostics, Basel, Switzerland) (data labeled as day 1, 2, 3).

For each sample, the data are expressed as a ratio of the level of LDH in wells containing cells transfected with anti-sense (AS) over the level of LDH in wells containing cells transfected with the reverse complement controls (RC) (ie:AS/RC). Thus, cells that become sensitized to drug will die and release LDH into the supernatant. An increase in the ratio signifies increased cell death and thus, higher levels of LDH in the media. A ratio higher than 1.5 signifies an effect of the anti-sense over the reverse complement control.

The data summarized in Table 3 demonstrates that neither KIA175–1182 nor KIA175–545 has an effect on the 184B5 normal breast epithelial cell line. By contrast, Table 4 shows that KIA175–545 sensitizes the MDA-MB-231 metastatic breast cancer cells to the effects of Cisplatin and to Campthesin (CPT). It did not appear to sensitize cells to the effects of Doxorubicin (Doxo). The data in Table 4 also shows that both anti-sense molecules alone caused an increase in cell death in this breast cancer cell line, suggesting that KIAA0175 may be targeted directly by inhibitors and such an inhibitor may be used therapeutically in the absence of other chemotherapeutic drugs.

TABLE 3

Effect of KIAA0175 Antisense −/+ Cisplatin on Normal Breast Epithelial Cell Line 184B5

| Day | Bcl2 AS (+ control) | KIA175-1182 | KIA175-545 | KIA175-545 + 7 μM Cisplatin |
|---|---|---|---|---|
| 0 | 0.0000 | 0.0000 | 0.0000 | 0.0000 |
| 1 | 1.2909 | 1.0223 | 1.1152 | 1.0691 |
| 2 | 1.5415 | 0.9065 | 1.1258 | 1.1928 |
| 3 | 1.3150 | 1.0663 | 1.2934 | 1.1284 |

TABLE 4

Effect of KIAA0175 Antisense −/+ Drug on Breast Cancer Cell Line MDA-MB-231

| Day | Bcl2 AS | KIA175-1182 | KIA175-545 | KIA175-545 + Cisplatin | KIA175-545 + Doxo | KIA175-545 + CPT |
|---|---|---|---|---|---|---|
| 0 | 1.03 | 0.76 | 0.84 | 0.71 | 0.89 | 0.79 |
| 1 | 1.04 | 2.04 | 1.05 | 1.10 | 1.05 | 1.12 |
| 2 | 2.2 | 1.67 | 1.37 | 1.72 | 1.39 | 1.69 |
| 3 | 2.23 | 1.52 | 1.62 | 1.95 | 1.34 | 1.88 |

Cis: Cisplatin; Doxo: Doxorubicin; CPT: Campihesin.

Example 10

Phosphorylation of KIAA0175 by ATM in Response to Gamma Irradiation

Ataxia telangiectasia mutated (ATM) is one of a subfamily of PI-3-like kinases and plays a central role in the DNA damage response. ATM is thought to primarily control the response to γ irradiation. The amino acid motifs SQ or TQ are the preferred sites of phosphorylation of ATM in many of its reported substrates, including p53, Chk2, Mdm2, etc. (Kim, S. T. et al., J. Biol. Chem. 1999 274(53):37538–43). KIAA0175 contains 3 SQ (Ser 100, Ser 125, Ser 391) sites.

GST-fusion proteins containing amino acids 42–182, 227–325, and 327–517 of KIAA0175 were expressed and purified from *Escherichia coli* and tested for their ability to act as substrate for ATM in vitro. Proteins were phosphorylated with ATM immunoprecipitates. A fusion including amino acids 327–517 harboring $S^{391}Q$ was a substrate for ATM. In contrast, phosphorylation of two other KIAA0175 fusions, amino acid 42–182 (containing $S^{100}Q$ and $S^{125}Q$) and amino acids 227–325 with no SQ sites, were not phosphorylated. In addition, KIAA0175 (327–517) phosphorylation was comparable to that seen with several known substrates of ATM included in the same assay, GST-p53 (1–106), GST-Chk2(1–222), and GST-hDM2 (330–491).

To further test whether KIAA0175 phosphorylation by ATM is regulated by DNA damage and to further map the putative site of phosphorylation, serine 391 was mutated to alanine. ATM immunoprecipitated from cells treated with γ-irradiation (IR) showed increased phosphorylation towards KIAA0175 (327–517) by 2–3 fold, similar to that observed with p53 or Chk2. Mutation of serine 391 to alanine completely abolished the irradiation induced phosphorylation by ATM. These results demonstrated that ATM can directly phosphorylate KIAA0175 in vitro in response to DNA damage and confirmed that the primary site of phosphorylation mapped to serine 391.

Those skilled in the art will recognize, or be able to ascertain, using no more than routine experimentation, many equivalents to the specific embodiments of the invention described herein. Such specific embodiments and equivalents are intended to be encompassed by the following claims.

All patents, published patent applications, and publications cited herein are incorporated by reference as if set forth fully herein.

What is claimed is:

1. An isolated KIAA0175 inhibitor wherein said inhibitor is an antisense molecule comprising the nucleic acid sequence of SEQ ID NO:1, wherein said antisense molecule is not longer than 25 nucleotides in length and is capable of inhibiting the expression of KIAA0175.

2. A composition comprising a therapeutically effective amount of at least one KIAA0175 inhibitor in a pharmaceutically acceptable carrier, wherein at least one of said KIAA0175 inhibitors is a polynucleotide comprising an antisense molecule of SEQ ID NO:1 wherein said polynucleotide is not longer than 25 nucleotides in length and hybridizes specifically with SEQ ID NO:9.

3. The composition of claim 2, comprising two or more KIAA0175 inhibitors.

4. The composition of claim 2 further comprising an inhibitor selected from the group consisting of an ATM inhibitor, a DNA-PK inhibitor and an ATR inhibitor.

* * * * *

SEQUENCE LISTING

<160> NUMBER OF SEQ ID NOS: 12

<210> SEQ ID NO 1
<211> LENGTH: 25
<212> TYPE: DNA
<213> ORGANISM: Artificial Sequence
<220> FEATURE:
<223> OTHER INFORMATION: Antisense Oligonucleotide

<400> SEQUENCE: 1
gaggtccctg tgagcatagc cctgg                                          25

<210> SEQ ID NO 2
<211> LENGTH: 25
<212> TYPE: DNA
<213> ORGANISM: Artificial Sequence
<220> FEATURE:
<223> OTHER INFORMATION: Antisense Oligonucleotide -continued

```
<400> SEQUENCE: 2
ggtcccgata cgagtgtccc tggag                                              25

<210> SEQ ID NO 3
<211> LENGTH: 25
<212> TYPE: DNA
<213> ORGANISM: Artificial Sequence
<220> FEATURE:
<223> OTHER INFORMATION: Antisense Oligonucleotide

<400> SEQUENCE: 3
tgcccatgct ccaaacatct gcctc                                              25

<210> SEQ ID NO 4
<211> LENGTH: 25
<212> TYPE: DNA
<213> ORGANISM: Artificial Sequence
<220> FEATURE:
<223> OTHER INFORMATION: Antisense Oligonucleotide

<400> SEQUENCE: 4
ctccgtctac aaacctcgta cccgt                                              25

<210> SEQ ID NO 5
<211> LENGTH: 25
<212> TYPE: DNA
<213> ORGANISM: Artificial Sequence
<220> FEATURE:
<223> OTHER INFORMATION: Antisense Oligonucleotide

<400> SEQUENCE: 5
gggtagcact ggcttgtcca cagga                                              25

<210> SEQ ID NO 6
<211> LENGTH: 25
<212> TYPE: DNA
<213> ORGANISM: Artificial Sequence
<220> FEATURE:
<223> OTHER INFORMATION: Antisense Oligonucleotide

<400> SEQUENCE: 6
aggacacctg ttcggtcacg atggg                                              25

<210> SEQ ID NO 7
<211> LENGTH: 27
<212> TYPE: DNA
<213> ORGANISM: Artificial Sequence
<220> FEATURE:
<223> OTHER INFORMATION: Primer for PCR amplification of KIAA0175

<400> SEQUENCE: 7
gggtatcagg aggcagcggc ttaaggg                                            27

<210> SEQ ID NO 8
<211> LENGTH: 30
<212> TYPE: DNA
<213> ORGANISM: Artificial Sequence
<220> FEATURE:
<223> OTHER INFORMATION: PRimer for PCR amplification of KIAA0175

<400> SEQUENCE: 8
aggctgtatc acacccacac tcatccggca                                         30

<210> SEQ ID NO 9
<211> LENGTH: 2470
```

<212> TYPE: DNA
<213> ORGANISM: Homo sapien

<400> SEQUENCE: 9

| | | | | | |
|---|---|---|---|---|---|
| ttggcgggcg | gaagcggcca | caacccggcg | atcgaaaaga | ttcttaggaa | cgccgtacca | 60 |
| gccgcgtctc | tcaggacagc | aggcccctgt | ccttctgtcg | ggcgccgctc | agccgtgccc | 120 |
| tccgcccctc | aggttctttt | tctaattcca | aataaacttg | caagaggact | atgaaagatt | 180 |
| atgatgaact | tctcaaatat | tatgaattac | atgaaactat | tgggacaggt | ggctttgcaa | 240 |
| aggtcaaact | tgcctgccat | atccttactg | gagagatggt | agctataaaa | atcatggata | 300 |
| aaaacacact | agggagtgat | tgccccggaa | tcaaaacgga | gattgaggcc | ttgaagaacc | 360 |
| tgagacatca | gcatatatgt | caactctacc | atgtgctaga | cagccaac | aaaatattca | 420 |
| tggttcttga | gtactgccct | ggaggagagc | tgtttgacta | tataatttcc | caggatcgcc | 480 |
| tgtcagaaga | ggagacccgg | gttgtcttcc | gtcagatagt | atctgctgtt | gcttatgtgc | 540 |
| acagccaggg | ctatgctcac | agggacctca | agccagaaaa | tttgctgttt | gatgaatatc | 600 |
| ataaattaaa | gctgattgac | tttggtctct | gtgcaaaacc | caagggtaac | aaggattacc | 660 |
| atctacagac | atgctgtggg | agtctggctt | atgcagcacc | tgagttaata | caaggcaaat | 720 |
| catatcttgg | atcagaggca | gatgtttgga | gcatgggcat | actgttatat | gttcttatgt | 780 |
| gtggatttct | accatttgat | gatgataatg | taatggcttt | atacaagaag | attatgagag | 840 |
| gaaaatatga | tgttcccaag | tggctctctc | cagtagcat | tctgcttctt | caacaaatgc | 900 |
| tgcaggtgga | cccaaagaaa | cggatttcta | tgaaaaatct | attgaaccat | ccctggatca | 960 |
| tgcaagatta | caactatcct | gttgagtggc | aaagcaagaa | tcctttttatt | cacctcgatg | 1020 |
| atgattgcgt | aacagaactt | tctgtacatc | acagaaacaa | caggcaaaca | atggaggatt | 1080 |
| taatttcact | gtggcagtat | gatcacctca | cggctaccta | tcttctgctt | ctagccaaga | 1140 |
| aggctcgggg | aaaaccagtt | cgtttaaggc | tttcttcttt | ctcctgtgga | caagccagtg | 1200 |
| ctaccccatt | cacagacatc | aagtcaaata | attggagtct | ggaagatgtg | accgcaagtg | 1260 |
| ataaaatta | tgtggcggga | ttaatagact | atgattggtg | tgaagatgat | ttatcaacag | 1320 |
| gtgctgctac | tccccgaaca | tcacagttta | ccaagtactg | gacagaatca | aatggggtgg | 1380 |
| aatctaaatc | attaactcca | gccttatgca | gaacacctgc | aaataaatta | agaacaaag | 1440 |
| aaaatgtata | tactcctaag | tctgctgtaa | agaatgaaga | gtactttatg | tttcctgagc | 1500 |
| caaagactcc | agttaataag | aaccagcata | agagagaaat | actcactacg | ccaaatcgtt | 1560 |
| acactacacc | ctcaaaagct | agaaaccagt | gcctgaaaga | aactccaatt | aaaataccag | 1620 |
| taaattcaac | aggaacagac | aagttaatga | caggtgtcat | tagccctgag | aggcggtgcc | 1680 |
| gctcagtgga | attggatctc | aaccaagcac | atatggagga | gactccaaaa | agaaagggag | 1740 |
| ccaaagtgtt | tgggagcctt | gaaggggggt | tggataaggt | tatcactgtg | ctcaccagga | 1800 |
| gcaaaaggaa | gggttctgcc | agagacgggc | ccagaagact | aaagcttcac | tataatgtga | 1860 |
| ctacaactag | attagtgaat | ccagatcaac | tgttgaatga | ataatgtct | attcttccaa | 1920 |
| agaagcatgt | tgactttgta | caaaagggtt | atacactgaa | gtgtcaaaca | cagtcagatt | 1980 |
| ttgggaaagt | gacaatgcaa | tttgaattag | aagtgtgcca | gcttcaaaaa | cccgatgtgg | 2040 |
| tgggtatcag | gaggcagcgg | cttaagggcg | atgcctgggt | ttacaaaaga | ttagtggaag | 2100 |
| acatcctatc | tagctgcaag | gtataattga | tggattcttc | catcctgccg | gatgagtgtg | 2160 |
| ggtgtgatac | agcctacata | aagactgtta | tgatcgcttt | gattttaaag | ttcattggaa | 2220 |

-continued

```
ctaccaactt gtttctaaag agctatctta agaccaatat ctctttgttt ttaaacaaaa    2280
gatattattt tgtgtatgaa tctaaatcaa gcccatctgt cattatgtta ctgtcttttt    2340
taatcatgtg gttttgtata ttaataattg ttgactttct tagattcact tccatatgtg    2400
aatgtaagct cttaactatg tctctttgta atgtgtaatt tctttctgaa ataaaaccat    2460
ttgtgaatat                                                           2470
```

<210> SEQ ID NO 10
<211> LENGTH: 651
<212> TYPE: PRT
<213> ORGANISM: Homo sapien

<400> SEQUENCE: 10

```
Met Lys Asp Tyr Asp Glu Leu Leu Lys Tyr Tyr Glu Leu His Glu Thr
  1               5                  10                  15

Ile Gly Thr Gly Gly Phe Ala Lys Val Lys Leu Ala Cys His Ile Leu
             20                  25                  30

Thr Gly Glu Met Val Ala Ile Lys Ile Met Asp Lys Asn Thr Leu Gly
         35                  40                  45

Ser Asp Leu Pro Arg Ile Lys Thr Glu Ile Glu Ala Leu Lys Asn Leu
     50                  55                  60

Arg His Gln His Ile Cys Gln Leu Tyr His Val Leu Glu Thr Ala Asn
 65                  70                  75                  80

Lys Ile Phe Met Val Leu Glu Tyr Cys Pro Gly Gly Glu Leu Phe Asp
                 85                  90                  95

Tyr Ile Ile Ser Gln Asp Arg Leu Ser Glu Glu Thr Arg Val Val
            100                 105                 110

Phe Arg Gln Ile Val Ser Ala Val Ala Tyr Val His Ser Gln Gly Tyr
        115                 120                 125

Ala His Arg Asp Leu Lys Pro Glu Asn Leu Leu Phe Asp Glu Tyr His
    130                 135                 140

Lys Leu Lys Leu Ile Asp Phe Gly Leu Cys Ala Lys Pro Lys Gly Asn
145                 150                 155                 160

Lys Asp Tyr His Leu Gln Thr Cys Cys Gly Ser Leu Ala Tyr Ala Ala
                165                 170                 175

Pro Glu Leu Ile Gln Gly Lys Ser Tyr Leu Gly Ser Glu Ala Asp Val
            180                 185                 190

Trp Ser Met Gly Ile Leu Leu Tyr Val Leu Met Cys Gly Phe Leu Pro
        195                 200                 205

Phe Asp Asp Asp Asn Val Met Ala Leu Tyr Lys Lys Ile Met Arg Gly
    210                 215                 220

Lys Tyr Asp Val Pro Lys Trp Leu Ser Pro Ser Ser Ile Leu Leu Leu
225                 230                 235                 240

Gln Gln Met Leu Gln Val Asp Pro Lys Lys Arg Ile Ser Met Lys Asn
                245                 250                 255

Leu Leu Asn His Pro Trp Ile Met Gln Asp Tyr Asn Tyr Pro Val Glu
            260                 265                 270

Trp Gln Ser Lys Asn Pro Phe Ile His Leu Asp Asp Cys Val Thr
        275                 280                 285

Glu Leu Ser Val His His Arg Asn Asn Arg Gln Thr Met Glu Asp Leu
    290                 295                 300

Ile Ser Leu Trp Gln Tyr Asp His Leu Thr Ala Thr Tyr Leu Leu Leu
305                 310                 315                 320

Leu Ala Lys Lys Ala Arg Gly Lys Pro Val Arg Leu Arg Leu Ser Ser
```

```
                    325                 330                 335
Phe Ser Cys Gly Gln Ala Ser Ala Thr Pro Phe Thr Asp Ile Lys Ser
            340                 345                 350
Asn Asn Trp Ser Leu Glu Asp Val Thr Ala Ser Asp Lys Asn Tyr Val
        355                 360                 365
Ala Gly Leu Ile Asp Tyr Asp Trp Cys Glu Asp Leu Ser Thr Gly
    370                 375                 380
Ala Ala Thr Pro Arg Thr Ser Gln Phe Thr Lys Tyr Trp Thr Glu Ser
385                 390                 395                 400
Asn Gly Val Glu Ser Lys Ser Leu Thr Pro Ala Leu Cys Arg Thr Pro
                405                 410                 415
Ala Asn Lys Leu Lys Asn Lys Glu Asn Val Tyr Thr Pro Lys Ser Ala
            420                 425                 430
Val Lys Asn Glu Glu Tyr Phe Met Phe Pro Glu Pro Lys Thr Pro Val
        435                 440                 445
Asn Lys Asn Gln His Lys Arg Glu Ile Leu Thr Thr Pro Asn Arg Tyr
    450                 455                 460
Thr Thr Pro Ser Lys Ala Arg Asn Gln Cys Leu Lys Glu Thr Pro Ile
465                 470                 475                 480
Lys Ile Pro Val Asn Ser Thr Gly Thr Asp Lys Leu Met Thr Gly Val
                485                 490                 495
Ile Ser Pro Glu Arg Arg Cys Arg Ser Val Glu Leu Asp Leu Asn Gln
            500                 505                 510
Ala His Met Glu Glu Thr Pro Lys Arg Lys Gly Ala Lys Val Phe Gly
        515                 520                 525
Ser Leu Glu Arg Gly Leu Asp Lys Val Ile Thr Val Leu Thr Arg Ser
    530                 535                 540
Lys Arg Lys Gly Ser Ala Arg Asp Gly Pro Arg Arg Leu Lys Leu His
545                 550                 555                 560
Tyr Asn Val Thr Thr Thr Arg Leu Val Asn Pro Asp Gln Leu Leu Asn
                565                 570                 575
Glu Ile Met Ser Ile Leu Pro Lys Lys His Val Asp Phe Val Gln Lys
            580                 585                 590
Gly Tyr Thr Leu Lys Cys Gln Thr Gln Ser Asp Phe Gly Lys Val Thr
        595                 600                 605
Met Gln Phe Glu Leu Glu Val Cys Gln Leu Gln Lys Pro Asp Val Val
    610                 615                 620
Gly Ile Arg Arg Gln Arg Leu Lys Gly Asp Ala Trp Val Tyr Lys Arg
625                 630                 635                 640
Leu Val Glu Asp Ile Leu Ser Ser Cys Lys Val
                645                 650

<210> SEQ ID NO 11
<211> LENGTH: 25
<212> TYPE: DNA
<213> ORGANISM: Artificial Sequence
<220> FEATURE:
<223> OTHER INFORMATION: Primer for PCR amplification of KIAA0175

<400> SEQUENCE: 11
tctgctgctg tcgacaacga gtgtc                                             25

<210> SEQ ID NO 12
<211> LENGTH: 25
<212> TYPE: DNA
<213> ORGANISM: Artificial Sequence
```

```
-continued

<220> FEATURE:
<223> OTHER INFORMATION: Primer for PCR amplification of KIAA0175

<400> SEQUENCE: 12
ccatagtgag gttgcatctg gtgcc                                              25
```